(12) United States Patent
Kenig et al.

(10) Patent No.: US 11,020,074 B2
(45) Date of Patent: Jun. 1, 2021

(54) METHODS AND SYSTEMS FOR UTILIZING 3D SENSORS IN NUCLEAR MEDICINE

(71) Applicant: MOLECULAR DYNAMICS LIMITED, Hamilton (BM)

(72) Inventors: Tal Kenig, Avihayil (IL); Uri Goldberg, Hod Hasharon (IL); Eli Stern, Givatayim (IL)

(73) Assignee: Molecular Dynamics Limited, Hamilton (BM)

( * ) Notice: Subject to any disclaimer, the term of this patent is extended or adjusted under 35 U.S.C. 154(b) by 176 days.

(21) Appl. No.: 16/321,791

(22) PCT Filed: Aug. 4, 2017

(86) PCT No.: PCT/EP2017/069832
§ 371 (c)(1),
(2) Date: Jan. 29, 2019

(87) PCT Pub. No.: WO2018/029111
PCT Pub. Date: Feb. 15, 2018

(65) Prior Publication Data
US 2020/0268333 A1    Aug. 27, 2020

Related U.S. Application Data

(60) Provisional application No. 62/371,850, filed on Aug. 8, 2016.

(51) Int. Cl.
*A61B 6/00* (2006.01)
*A61B 5/00* (2006.01)

(52) U.S. Cl.
CPC ............ *A61B 6/469* (2013.01); *A61B 5/0064* (2013.01); *A61B 5/0077* (2013.01); *A61B 6/547* (2013.01)

(58) Field of Classification Search
CPC ..... A61B 6/469; A61B 5/0064; A61B 5/0077; A61B 6/547; A61B 6/545; A61B 6/0407; A61B 6/102; A61B 6/4266; A61B 6/037
See application file for complete search history.

(56) References Cited

U.S. PATENT DOCUMENTS

| | | | | |
|---|---|---|---|---|
| 5,376,796 A | * | 12/1994 | Chan ................. | G01B 11/2433 250/363.02 |
| 2013/0261446 A1 | | 10/2013 | Paladini | |
| 2015/0327831 A1 | * | 11/2015 | Levin .................... | A61B 6/037 600/427 |

OTHER PUBLICATIONS

International Search Report PCT/EP2017/069832 prepared by the European Patent Office completion date Nov. 28, 2017, 5 pages.

* cited by examiner

*Primary Examiner* — David P Porta
*Assistant Examiner* — Meenakshi S Sahu
(74) *Attorney, Agent, or Firm* — Brooks Kushman P.C.

(57) ABSTRACT

Described are methods and systems for scanning at least a portion of a patient with a gamma detector mounted on an arm extending towards the patient. One described method includes: obtaining data indicative or coordinates of points on the outer surface of the patient; determining a target position for the gamma detector based on the data indicative, of the coordinates; and causing the gamma detector to detect gamma radiation from the patient when the gamma detector is at the target position.

27 Claims, 9 Drawing Sheets

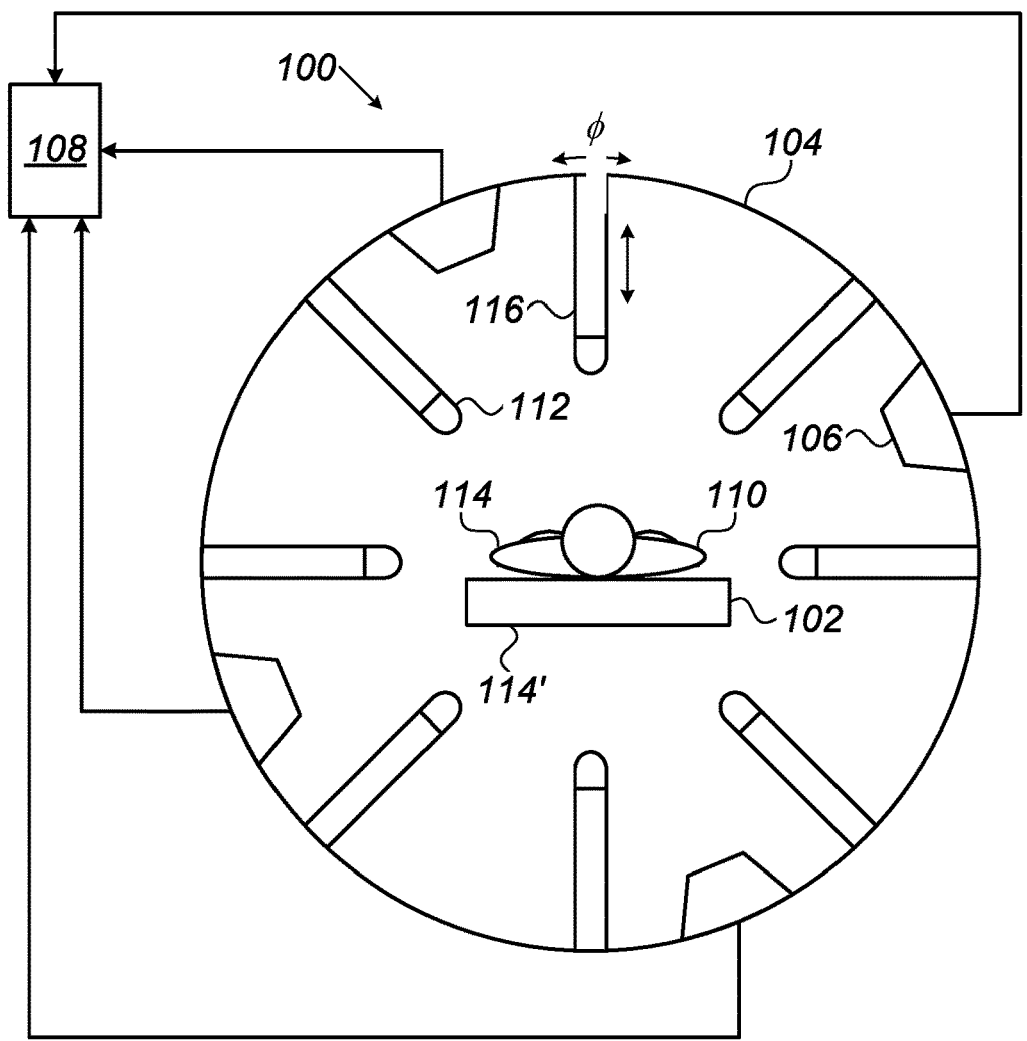
FIG. 1C
FIG. 2
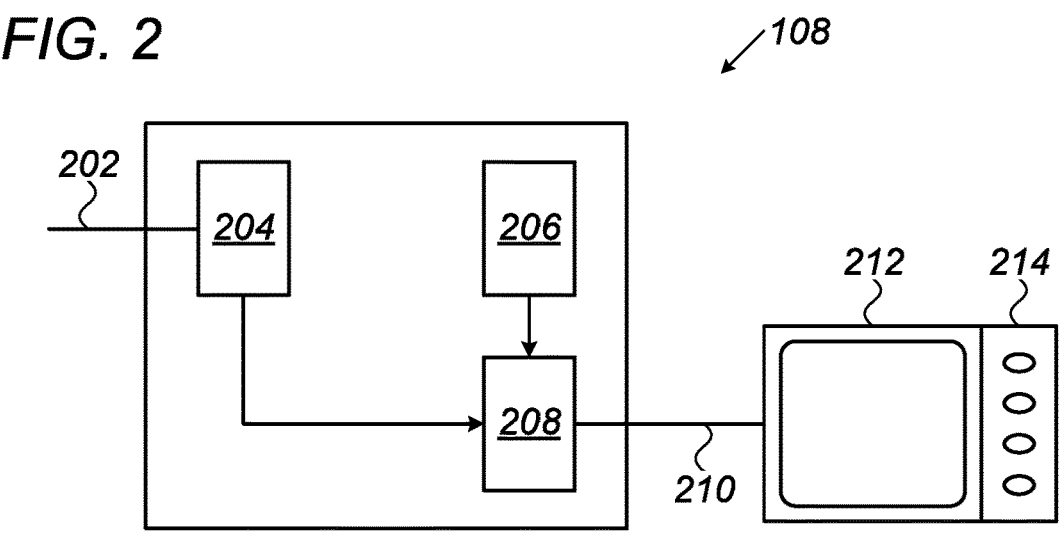

METHODS AND SYSTEMS FOR UTILIZING 3D SENSORS IN NUCLEAR MEDICINE

CROSS-REFERENCE TO RELATED APPLICATION

This application is the U.S. national phase of PCT Application No. PCT/EP2017/069832 filed on Aug. 4, 2017, which claims the benefit of U.S. Provisional Patent Application No. 62/371,850 filed on Aug. 8, 2016, the disclosures of which are incorporated in their entirety by reference herein.

FIELD AND BACKGROUND OF THE INVENTION

The present invention, in some embodiments thereof, relates to method and system of imaging and, more particularly, but not exclusively, to method and system of medical imaging.

Volumetric scans such as SPECT scans, PET scans, CT scans, MRI scans, Ultrasound scans, and the like are commonly used, mostly in the medical industry, to observe the inner parts of objects that would otherwise be unobservable non-destructively. A conventional volumetric scan is intended to produce a volumetric image of a volume of the body.

SUMMARY OF THE INVENTION

Some embodiments of the present invention include a method of scanning at least a portion of a patient with a gamma detector mounted on an arm extending towards the patient. The method comprising:

obtaining data indicative of coordinates of points on the outer surface of the patient;

determining a target position for the gamma detector based on the data indicative of the coordinates; and causing the gamma detector to detect gamma radiation from the patient when the gamma detector is at the target position.

In some embodiments, the arm extends along a specified direction, and obtaining the data comprises obtaining data indicative of a distance between the gamma detector and a point on the outer surface of the patient along the specified direction.

In some embodiments, the method includes causing the detector to move to the target position.

In some embodiments, causing the detector to move to the target position comprises causing the arm to extend towards the patient.

In some embodiments, determining a target position comprises determining a plurality of target positions for the gamma detector.

In some embodiments, the method includes causing the detector to move from one of the plurality of target positions to the other.

In some embodiments, the method includes causing the detector to move from one of the plurality of target positions to the other and detect gamma radiation during the movement.

In some embodiments, causing the gamma detector to detect gamma radiation from the patient comprises causing the gamma detector to detect gamma radiation from the patient at each of the plurality of target positions determined.

In some embodiments, determining a plurality of target positions comprises determining a range of directions from which the arm extends towards the patient.

In some embodiments, the method may include moving the gamma detector continuously along said range of directions, and causing the gamma detector to detect gamma radiation during said moving.

In some embodiments, determining the target position comprises determining a target swivel angle between said detector and the arm on which the detector is mounted.

In some embodiments, causing the gamma detector to detect gamma radiation from the patient at the target position comprises causing the gamma detector to change a swivel angle between the detector and the arm on which the detector is mounted.

In some embodiments, determining the target position comprises determining a target direction for the arm to be extended towards the patient.

In some embodiments, the method includes causing a change in the direction along which the arm is extended and detect gamma radiation from a plurality of directions.

In some embodiments, the target position determined is characterized by a target distance between the detector and the patient along the target direction.

Some embodiments of the present invention include a method of scanning at least a portion of a patient with a gamma detector mounted on an arm extending towards the patient along a specified direction, the method comprising:

obtaining data indicative of a distance between the gamma detector and the patient along said specified direction;

determining a target direction for the arm based on the data indicative of the distance;

causing the arm to move to the target direction;

obtaining data indicative of a distance between the gamma detector and the patient along said target direction;

determining a target position for the gamma detector based on the data indicative of the distance along the target direction; and causing the gamma detector to detect gamma radiation from the patient at the target position.

In some embodiments, determining the target position comprises determining a target distance between the detector and the patient along the specified direction.

In some embodiments, obtaining the data indicative of the distance comprises obtaining data received from at least one 3D sensor.

In some embodiments, the scanning of the at least a portion of the patient is with two or more gamma detectors, each mounted on a respective arm extending towards the patient along a respective specified direction, and the method includes:

obtaining for each of the gamma detectors data indicative of a distance from the patient along the respective specified direction;

determining for each of the gamma detectors a respective target position based on the data indicative of at least some of the distances; and causing each of the gamma detectors to detect gamma radiation from the patient at the respective target position.

In some embodiments, the scanning of the at least a portion of the patient is with two or more gamma detectors supported by a common gantry, and causing a gamma detector to detect gamma radiation from the patient at a target position comprises rotating the gantry.

In some embodiments, the scanning of the at least a portion of the patient is with two or more gamma detectors supported by a common gantry, and causing a gamma detector to detect gamma radiation from the patient at a target position comprises moving the patient in respect to the gantry and/or moving the gantry in respect to the patient.

In some embodiments, determining a target position for the gamma detector comprises generating an approximation to the outer surface of the patient based on the data indicative of the distance between the gamma detector and the patient along the specified direction.

In some embodiments, the gamma detectors are caused to detect the gamma radiation from the patient simultaneously at the respective target positions.

In some embodiments, each gamma detector is in a respective detection head, and the target position of each gamma detector is determined in consideration of target positions of other gamma detectors to ensure that the detection heads do not collide with each other.

In some embodiments, the method includes receiving data indicative of the kind of image to be taken, and wherein the target position for the gamma detector is determined based on the data indicative of the distance and the data indicative of the kind of image to be taken.

Some embodiments of the present invention may include an apparatus for scanning at least a portion of a patient, the apparatus comprising:
 a gamma detector mounted on an end of an arm extending towards the patient support along a specified direction;
 a patient support; and
 a processor configured to:
  obtain data indicative of a distance between the gamma detector and the patient along said specified direction;
  determine a target position for the gamma detector based on the data indicative of the distance; and
  cause the gamma detector to detect gamma radiation from the patient at the target position.

In some embodiments, the arm is extendible.

In some embodiments, the processor is configured to determine a plurality of target positions for the gamma detector.

In some embodiments, the processor is configured to cause the gamma detector to detect gamma radiation from the patient at each of the plurality of target positions.

In some embodiments, the plurality of target positions include a range of directions from which the arm extends towards the patient.

In some embodiments, the processor is configured to cause the gamma detector to move continuously along said range of directions and detect gamma radiation during the movement.

In some embodiments, the target position comprises a target swivel angle between the detector and the arm.

In some embodiments, the processor is configured to cause the gamma detector to change a swivel angle between the detector and the arm based on the data indicative of the distance.

In some embodiments, the processor is configured to determine, based on the data indicative of the distance, a target direction for the arm.

In some embodiments, the processor is configured to cause a change in the direction along which the arm is extended based on the data indicative of the distance.

In some embodiments, the processor is configured to determine based on the data indicative of the distance a target distance between the detector and the patient along the target direction.

In some embodiments, the processor is configured to determine a target distance between the detector and the patient along the specified direction.

In some embodiments the processor is configured to obtain the data indicative of the distance by processing data received from at least one 3D sensor.

In some embodiments, the apparatus further includes the at least one 3D sensor.

In some embodiments, the apparatus includes two or more gamma detectors, each mounted on a respective arm extending towards the patient along a respective specified direction, and wherein the processor is configured to:
 obtain, for each of the gamma detectors, data indicative of a distance from the patient along the respective specified direction;
 determine, for each of the gamma detectors, a respective target position based on the data indicative of the distances; and
 cause each of the gamma detectors to detect gamma radiation from the patient at the respective target position.

In some embodiments, the apparatus includes two or more gamma detectors supported by a common gantry, and the processor is configured to cause the gantry to rotate to allow a gamma detector to detect gamma radiation from a direction different from the respective specified direction.

In some embodiments, the apparatus includes two or more gamma detectors supported by a common gantry, and the processor is configured to cause movement of the patient support in respect to the gantry and/or cause movement of the gantry in respect to the patient support based on the data indicative of the distance.

In some embodiments, the processor is configured to generate an approximation to the outer surface of the patient based on the data indicative of the distance between the gamma detector and the patient along the specified direction, and determine the target position based on the approximation.

In some embodiments, the processor is configured to cause the gamma detectors to detect the gamma radiation from the patient simultaneously at the respective target position.

In some embodiments, each gamma detector is in a respective detection head, and the processor is configured to determine the target position of each gamma detector considering target positions of other gamma detectors to ensure that the detection heads do not collide.

In some embodiments, the processor is configured to receive data indicative of the kind of image to be taken, and determine the target position for the gamma detector based on the data indicative of the distance and the data indicative of the kind of image to be taken.

An aspect of some embodiments of the invention includes a system for medical imaging a region of interest. A region of interest may also be referred to herein as a region to be imaged. The system may include:
 a support, for supporting at least a portion of a patient's body;
 a gantry, supporting a gamma detector,
 a 3D sensor; and
 a processor,
wherein
 the processor is configured to:
 determine a region to be imaged;
 receive from the 3D sensor coordinates of at least one point of an outer surface of the patient, the support, or both the patient and the support; and determine at least one parameter affecting an arrangement of the gamma detectors in respect to the region to be imaged based on the coordinates of the at least one point.

In some embodiments, the at least one parameter comprises a position of the support in respect to the gantry.

In some embodiments, the at least one parameter comprises a gantry angle of a gantry supporting the detectors.

In some embodiments, the at least one parameter comprises a plurality of gantry angles.

In some embodiments, the processor is further configured to determine, based on the indication of the kind of image to be taken and the coordinates of the at least one point, a dwelling time for each of said plurality of gantry angles.

In some embodiments, the at least one parameter comprises a range of gantry angles.

In some embodiments, the processor is further configured to determine, based on the indication of the kind of image and the coordinates of the at least one point, a pace for moving the gantry along the range of gantry angles.

In some embodiments, the processor is configured to determine, based on the indication of the kind of image and the coordinates of the at least one point, a plurality of different paces, each for moving the gantry along a sub-range of the range of gantry angles.

In some embodiments, each of said gamma detectors is mounted on an arm extendable from the gantry.

In some embodiments, each of said gamma detectors is arranged to swivel in respect to an arm connecting the gamma detector to the gantry.

In some embodiments, the at least one parameter includes a swivel angle of the detector in respect to the arm for at least one of the detectors.

In some embodiments, the at least one parameter includes a plurality of swivel angles of the detector in respect to the arm for at least one of the detectors.

In some embodiments, the at least one parameter includes a range of swivel angles of the detector in respect to the arm for at least one of the detectors.

In some embodiments, the processor is further configured to determine, based on the indication of the kind of image and the coordinates of the at least one point, a pace for moving the detector along the range of swivel angles.

In some embodiments, the at least one parameter includes an amount of extension of at least one extendable arm connecting a gamma detector to the gantry.

In some embodiments, the processor is configured to generate, based on the coordinates of the at least one point, a model of the outer surface of the patient, the support, or both the patient and the support, and determine the at least one parameter based on a location of the region to be imaged in respect to the model.

In some embodiments, the processor is configured to determine the at least one parameter affecting the arrangement of the gamma detectors in respect to the region of interest based on a location of the region of interest in respect to the model of the outer surface of the patient and/or support.

An aspect of some embodiments of the inventions includes a method of imaging a region of interest in a patient by a medical imaging device for imaging a patient supported by a patient support, the medical imaging device comprising a gantry and a plurality of gamma detectors supported on the gantry, the method comprising:

receiving an indication of the kind of image to be taken;

receiving coordinates of at least one point of an outer surface of the patient, the support, or both the patient and the support;

determining at least one parameter affecting an arrangement of the gamma detectors in respect to the region of interest based on the indication of the kind of image and the coordinates of the at least one point; and controlling the gamma detectors, the gantry, and/or the support in accordance with the at least one parameter determined.

In some embodiments, the at least one parameter comprises a position of the support in respect to the gantry.

In some embodiments, the at least one parameter comprises a gantry angle of a gantry supporting detectors in respect to an axis of the gantry.

In some embodiments, the at least one parameter comprises a plurality of gantry angles.

In some embodiments, the method includes determining, based on the indication of the kind of image to be taken and the coordinates of the at least one point, a dwelling time for each of said plurality of gantry angles.

In some embodiments, the at least one parameter comprises a range of gantry angles.

In some embodiments, the method includes determining, based on the indication of the kind of image to be taken and the coordinates of the at least one point, a pace for moving the gantry along the range of gantry angles.

In some embodiments, each of said gamma detectors is mounted on an arm extendable from the gantry.

In some embodiments, each of said gamma detectors is mounted on an arm extendable from the gantry so that the gamma detector may swivel in respect to the arm.

In some embodiments, the at least one parameter includes a swivel angle of the detector in respect to the arm for at least one of the detectors.

In some embodiments, the at least one parameter includes a plurality of swivel angles of the detector in respect to the arm for at least one of the detectors.

In some embodiments, the at least one parameter includes a range of swivel angles of the detector in respect to the arm for at least one of the detectors.

In some embodiments, the method further includes determining, based on the indication of the kind of image and the coordinates of the at least one point, a pace for moving the detector along the range of swivel angles.

In some embodiments, n the at least one parameter includes an amount of extension of at least one extendable arm connecting a gamma detector to the gantry.

In some embodiments, the method includes generating, based on the coordinates of the at least one point, a model of the outer surface of the patient, the support, or both the patient and the support, and determining the at least one parameter based on a location of the region to be imaged in respect to the model.

In some embodiments, the method includes determining the at least one parameter affecting the arrangement of the gamma detectors in respect to the region of interest based on a location of the region of interest in respect to the model of the outer surface of the patient and/or support.

Some embodiments of the present invention includes a system for performing medical imaging of a region of interest, the system comprising:

a support for supporting at least a portion of a patient's body;

a gantry which supports multiple gamma detectors;

a 3D sensor configured to sense a point of an contour of a portion of the patient; and a processor configured to determine a desired position of the support in respect to the gantry based on data obtained by the 3D sensor.

In some embodiments, the processor comprises:
an input configured to receive data indicative of an contour of at least a portion of the patient sensed by the 3D sensor;
a memory storing instructions for determining a desired position of the support in respect to the gantry based on the data received by the input; and
an output.

In some embodiments, the output is configured to indicate to a user a desired position determined by executing the instructions.

In some embodiments, the output is configured to control the position of the support in respect to the gantry based on a desired position determined by executing the instructions.

In some embodiments, the system includes a user interface allowing a user to indicate a kind of scan to be performed, wherein the processor is configured to determine the desired position of the support in respect to the gantry based on results obtained by the 3D sensor and the kind of scan indicated by the user.

In some embodiments, the 3D sensor is installed on said gantry.

In some embodiments, the desired position of the support in respect to the gantry includes a vertical position of the support in the gantry.

In some embodiments, the desired position of the support in respect to the gantry includes a horizontal position of the support in the gantry along a longitudinal axis of the patient.

In some embodiments, the processor is configured to determine the desired position of the support in respect to the gantry based on:
results obtained by the 3D sensor, and
a non-diagnostic scan of a portion of the patient scanned by the system, said portion comprising the region to be imaged.

In some embodiments, the 3D sensor is configured to generate a point cloud indicative of the position of an contour of a portion of the patient, the support, or both the patient and the support.

In some embodiments, the 3D sensor is one of a plurality of 3D sensors, and the processor is configured to determine the desired position of the support in respect to the gantry based on data obtained by the plurality of 3D sensors.

In some embodiments, the processor is configured to estimate an approximate contour of the patient and the support based on input from the plurality of 3D sensors.

Some embodiments of the present invention include a method of automatically determining a desired position of a support carrying a patient in respect to a gantry that supports multiple gamma detectors for imaging the patient, the method comprising:
receiving from a user interface indication of a portion of the patient to be scanned;
receiving, from at least one 3D sensor, data indicative of spatial coordinates of a contour of the patient and the support; and
determining the desired position of the support based on the indication and the data.

In some embodiments, the method further includes:
receiving through the user interface an instruction to bring the support to the desired position determined; and
controlling the support to move to the desired position determined in response to receiving the instruction.

In some embodiments, determining the desired position of the support comprises combining the data received from the 3D sensor with a non-diagnostic image data of a portion of the patient supported by the support.

In some embodiments, the method includes:
scanning a portion of the patient supported by the support to obtain non-diagnostic image data of said portion of the patient; and
combining the data received from the 3D sensor with the non-diagnostic image data to determine the desired position of the support.

In some embodiments, the method includes
sending a control signal to the at least one 3D sensor to collect data pertaining to the patient on the support, and
determining the desired position of the support based on a point cloud indicative of the position of a contour of a portion of the patient produced in response to said control signal.

Some embodiments of the invention include a system for generating a scanning plan for medical imaging of at least a portion of a patient, the system comprising:
a support for supporting at least a portion of a patient's body;
a gantry which supports multiple gamma detectors;
at least one 3D sensor configured to sense at least one point of an outer surface of a portion of the patient; and
a processor configured to receive information comprising:
an indication of a region to be imaged; and
data indicative of the location of the at least one point sensed by the at least one 3D sensor, and
generate a scanning plan for the medical imaging based on information received.

In some embodiments, the at least one 3D sensor is configured to generate a point cloud indicative of the position of an outer surface of at least one of: a portion of the patient, a portion of a support supporting the patient during the medical imaging, or portions of both the patient and the support.

In some embodiments, the system includes a plurality of 3D sensors, and the processor is configured to generate the scanning plan based on data sensed by the plurality of 3D sensors.

In some embodiments, the processor is configured to estimate an approximate contour of the patient and the support based on input from the at least one 3D sensor.

In some embodiments, the processor comprises:
an input configured to receive data indicative of at least one point of an outer surface of at least a portion of the patient sensed by the at least one 3D sensor; and
a memory storing instructions for generating the scanning plan based on the data received by the input.

In some embodiments, at least one of the at least one 3D sensor is installed on said gantry.

In some embodiments, each of the gamma detectors is connected to the gantry by an extendable arm so that the detector can swivel in respect to the extendable detector arm.

In some embodiments, the scanning plan includes a number of gantry positions and corresponding gantry angles.

In some embodiments, the scanning plan includes a dwell time for each of said gantry positions, at least two of said dwell times being different from each other.

In some embodiments, the scanning plan includes a plurality of swivel angles for at least one of the detectors.

In some embodiments, the scanning plan includes a dwell time for each of said swivel angles, at least two of said dwell times being different from each other.

In some embodiments, the scanning plan includes a first and second gantry positions and a rate of advancing the gantry between said first and second gantry positions.

In some embodiments, the scanning plan includes a plurality of rates, each of advancing the gantry along a portion of a path between the first and second gantry positions.

In some embodiments, the scanning plan includes a positioning of the support in respect to the gantry.

In some embodiments, the system includes a user interface configured to receive from a user indication as to the kind of scan to be planned, and the processor is configured to generating the scanning plan based on said indication and the input from the at least one 3D sensor.

Some embodiments of the present invention include a method of planning a scan of a region residing in a portion of a patient by a medical imaging device comprising a support at least for the portion of the patient and a gantry supporting multiple gamma detectors, the method comprising:

receiving, from a 3D sensor, data pertaining to spatial coordinates of a point of an outer surface of the portion of the patient;

receiving a non-diagnostic image of the portion of the patient;

receiving indication to a region of special interest within the region imaged in the non-diagnostic image;
and planning the scan based on the location of the region to be imaged and the region of special interest in respect to the contour of the patient.

In some embodiments, receiving from the 3D sensor data pertaining to spatial coordinates of points composing a point cloud indicative of the position of an contour of a portion of the patient, the support, or both the patient and the support.

In some embodiments, receiving data from a plurality of 3D sensors, planning the scan based on data obtained by the plurality of 3D sensors.

In some embodiments, the method includes estimating an approximate contour of the patient and the support based on input from the plurality of 3D sensors.

In some embodiments, the 3D sensor is installed on the gantry.

In some embodiments, each of the gamma detectors is connected to the gantry by an extendable detector arm so that the detector can swivel in respect to the extendable detector arm.

In some embodiments, the planning includes determining a number of gantry positions and corresponding gantry angles.

In some embodiments, the scanning plan includes a dwell time for each of said gantry positions, at least two of said dwell times being different from each other.

In some embodiments, the detectors are configured to swivel, and the scanning plan includes a plurality of swivel angles for at least one of the detectors.

In some embodiments, planning the scan comprises determining a dwell time for each of said swivel angles, at least two of said dwell times being different from each other.

In some embodiments, the scanning plan includes a first and second gantry positions and a rate of advancing the gantry between said first and second gantry positions.

In some embodiments, the scanning plan includes a first and second swivel angle for at least one detector and a rate of advancing the detector between said first and second swivel angles.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

As used herein, the term "processor" may include an electric circuit that performs a logic operation on input or inputs. Whenever a processor is mentioned, it may be embodied in a single processor, or in a plurality of processors. A processor may include one or more integrated circuits, microchips, microcontrollers, microprocessors, all or part of a central processing unit (CPU), graphics processing unit (GPU), digital signal processors (DSP), field-programmable gate array (FPGA) or other circuit suitable for executing instructions or performing logic operations. The instructions executed by the processor may, for example, be pre-loaded into the processor or may be stored in a separate memory unit such as a RAM, a ROM, a hard disk, an optical disk, a magnetic medium, a flash memory, other permanent, fixed, or volatile memory, or any other mechanism capable of storing instructions for the processor. The processor(s) may be customized for a particular use, or can be configured for general-purpose use and can perform different functions by executing different software.

If more than one processor is employed, all may be of similar construction, or they may be of differing constructions electrically connected or disconnected from each other. They may be separate circuits or integrated in a single circuit. When more than one processor is used, they may be configured to operate independently or collaboratively. They may be coupled electrically, magnetically, optically, acoustically, mechanically or by other means permitting them to interact.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1C is a diagrammatic illustration of a system for performing medical imaging of a region of interest according to some embodiments of the invention;

FIG. 2 is a simplified block diagram of a processor configured to carry out methods described herein;

DESCRIPTION OF EMBODIMENTS OF THE INVENTION

Overview

Figure 1A:
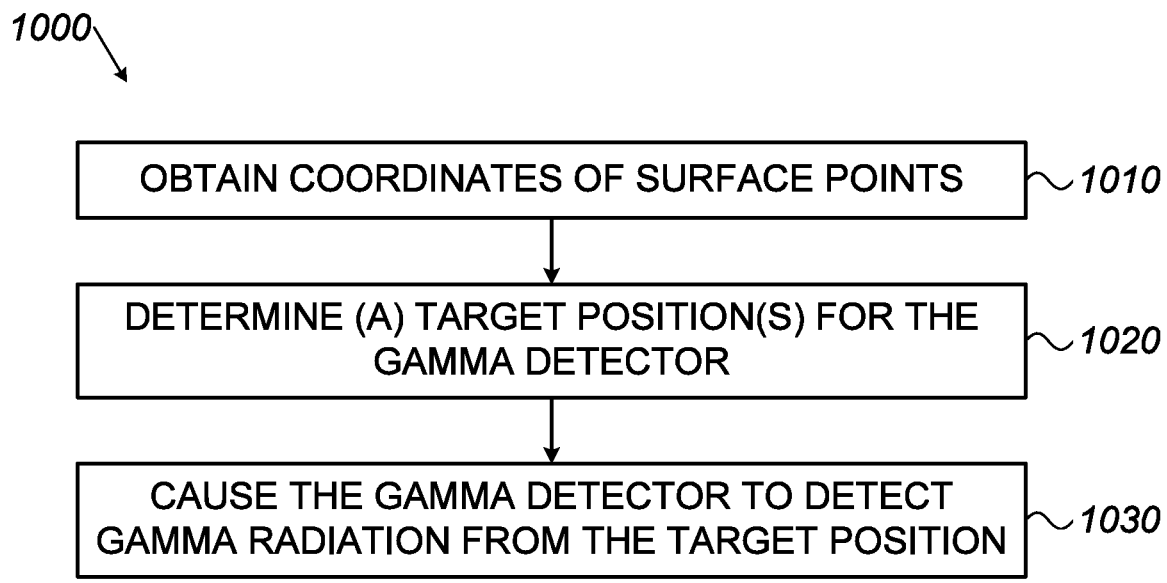
FIG. 1A is a flowchart of a method of scanning at least a portion of a patient according to some embodiments of the invention.

The present invention, in some embodiments thereof, relates to methods and systems of imaging and, more particularly, but not exclusively, to methods and systems of medical imaging.

In some embodiments of the invention, the imaging is single photon emission computed tomography (SPECT). In typical SPECT imaging, the patient is administered with agents that emit gamma photons and bind preferentially to specific tissues, and the image is acquired by detecting gamma photons emitted from within a region in the body of the patient, and assigning each of the detected photons a direction from which it emerged, or a plurality of directions, each associated with a probability that this is the direction from which the photon emerged. The data on received photons, emerging directions, and associated probabilities may be used for reconstructing an image of the region in the body of the patient.

Assigning each of the detected photons a probability that it emerged from a specific direction may be accomplished using a collimator having one side facing the imaged body, and another side facing a gamma detector. The collimator may include any structure that limits the directions from which photons may arrive at the gamma detector. For example, a parallel hole collimator is a structure that includes a lot of parallel gamma absorbing partitions that define cells in between them. The cells may have a rectangular cross-section, hexagonal cross-section, circular cross-section, or a cross section of any other shape. A gamma photon that hits one of those partitions is usually absorbed in the partition, so that mainly photons that go in parallel to the partitions, along a cell, reach the detector. This way, each photon that reaches the gamma detector is associated with a high probability to emerge from a location along a line parallel to the collimator's cells, and lower probabilities to emerge from other directions. The specific probabilities may depend on the size of cells, the thickness of the walls, and the absorption coefficient of the wall. The gamma detector may include a plurality of detection cells, e.g., one for every collimator cell, so that the location at which the photon meets the detector may also be known.

In some embodiments, there are many gamma detectors (e.g., 4, 5, 6, 8, 12, 16, or intermediate number), each in a respective detection head. A detection head may include a detector, electronics configured to indicate whenever a photon is received at the detector and where on the detector the photon is received, and a collimator. The detection heads may be supported on a frame (a/k/a gantry) carrying them. In some embodiments, there is a common frame, common to all the detection heads. In some embodiments, there may be two or more frames, each supporting one or more of the detection heads. During imaging, a portion of the patient that has to be imaged is supported on a patient support, and the detectors are brought as close as possible to the patient outer surface so as to allow for maximal possible resolution of the images reconstructed from the readings of the detector.

In some embodiments, the imaging may take place without a gantry. For example, the detectors may be mounted on separate arms that are not supported on a common frame, but controlled to move cooperatively, so their movement to and from the patient brings each of the detectors to a requisite position in respect to the region to be imaged.

The exact arrangement of the detectors in respect to the region to be imaged may determine to a large extent the image resolution, and the intensity of radiation collected at a given imaging time.

An aspect of some embodiments of the invention includes scanning a patient by gamma radiation using data indicative of coordinates of surface points of the patient. For example, the data may be indicative of a distance between a gamma detector and the patient. This distance may be used for determining a target position for the detector, from which it would be desired to detect the gamma radiation. In some embodiments, determining a target position for a gamma detector based on data indicative of coordinates of one or more points on the outer surface of the patient and/or support may include determining a position at which the distance between the detector and the patient (or support) outer surface is minimal, so as to be as close as possible to the patient, while not touching the patient.

For example, if the gamma detector can approach the patient along some specified direction, the target position may be along that direction, as close as possible to the patient without touching the patient. For example, if the gamma detector is mounted on an arm extendable from a gantry towards the patient, the specified direction may be the extension direction of the arm. If the current distance between the patient and the detector is 30 cm, the target position may be 29 cm closer to the patient, along the specified direction.

In some embodiments, it may be desirable to detect the radiation from many different directions. In some embodiments, the number of different angular positions from which gamma radiation is to be detected, and in some embodiments also the angular positions themselves may be determined based on coordinates of at least one point on a surface of the patient, or the patient and the support. For example, the coordinates of the surface point(s) may be used to estimate an outer shape of the patient and support, and the number of angular positions (and the angular positions themselves) may be determined so that gamma radiation is collected from as many locations within the patient and in a sufficient number of direction to allow satisfactory reconstruction of the image (e.g., sufficient to span 180°) at minimal scanning time. While reference is usually made herein to at least one point on the surface, more than one point may be advantageous. For example, two, four, six, or eight points may usually allow better modelling of the outer surface, and therefore also better determination of target position of detectors, or other parameters to be determined for a scanning plan. Point clouds comprising hundreds of points may even be better, in some embodiments. However, in some embodiments, the accuracy obtained from one point, for example using a spatial model of the (or a typical) patient and/or the support, may be sufficient. The number of different angular positions from which gamma radiation is to be detected, and the angular positions themselves, may depend on coordinates of points on the surface of the patient. For example, such coordinates may be indicative of a cylinder that has large enough a radius to encompass the entire patient portion to be imaged, but small enough to nearly touch the patient. Now, when this radius is large (e.g., for imaging the abdomen of a large patient), there may be a need to detect from more angular positions than when this radius is small (e.g., for imaging a head or a knee of a patient). Thus, the coordinates of one target position may be indicative to the radius of the cylinder, and be used to determine a number of target positions for the detector. It is noted that the cylinder in this example may be replaced by any other shape that may be large enough to encompass the patient portion to be imaged and small enough to nearly touch the patient or the patient support.

In yet another example of scanning a patient using data indicative of coordinates of surface points of the patient, swivel angles may be considered. In some embodiments, the gamma detector is mounted on an arm so that the detector can swivel around one or more axes attached to the arm to change the field of view of the detector without moving the arm. In some embodiments, the field of view encompasses all points of the patient viewable from a given position of the arm. However, in some cases, swiveling the detector may bring into the field of view of the detector areas outside the patient. Limiting the swivel only to angles at which at least a portion of the patient is within the field of view of the detector may save scanning time, and/or improve image quality obtainable in a given scanning time. Thus, in some embodiments, the coordinates of at least one point on the surface of the patient may be used to estimate the general shape of the patient and the support, for example using a spatial model of the (or a typical) patient and/or the support, and swivel angles may be determined based on this estimate so that the detectors swivel only through angles where at least a portion of the field of view is occupied by a portion of the patient. In some embodiments, this requirement may be more restrictive, for example, that at least half of the field of view will have in it a portion of the ROI. This exemplifies a way by which information indicative of coordinates of surface points of the patient may be used to determine the limits of the swiveling of the detector.

In some embodiments, the scanning method may include obtaining data indicative of the distance between the detector and the patient along two or more directions. For example, in some embodiments, data indicative of the distance between the patient and the detector may be obtained when the detector is aimed at the patient along a first direction (e.g., the direction referred to herein as a specified direction). Based on this data, it may be determined that detection should take place when the detector is aimed at the patient along a second direction (e.g., the direction referred to herein as a target direction). Once the detector is at the second position, it sometimes may be useful to obtain information indicative of its distance from the patient along the second direction. While this information could have, in some embodiments, been estimated (e.g., approximated) based on the data indicative of the distance between the detector and the patient along the first direction, a measurement devoted for obtaining information indicative of the distance along the second direction may be more accurate than the estimation made before. The new data may be useful in determining a target position for the detector in greater accuracy than could have been possible using the data obtained regarding the distance along the first direction.

The data indicative of the distance between the detector and the patient along the specified direction (or along any other direction) may be obtained from a 3D sensor, and may include data indicative of coordinates of one or more points on the outer surface of the patient. In some embodiments, the data may be obtained from a plurality of 3D sensors. As more 3D sensors are employed, more data may be obtained in a given time. For example, data obtained from a single 3D sensor moved to sense the patient from 6 different directions may be obtained by six sensors at less than a sixth of the time, if the sensing is carried out simultaneously from 6 directions, and time spent on moving a sensor from one viewing direction to another is saved. In some embodiments, the saving may be smaller because not all the sensors work together, to omit cross-talk problems or the like.

In some embodiments, the scanning may take place using a plurality of gamma detectors. In some such embodiments, the gamma detectors detect the gamma radiation from the patient simultaneously, each from a respective target position. In some embodiments, each gamma detector is in a respective detection head, and the target position of each gamma detector is determined in consideration of target positions of other gamma detectors to ensure that the detection heads do not collide with each other.

Each gamma detector may be mounted on a respective arm that extends along a respective specified direction. In some embodiments, each arm may also be extendible along the respective specified direction, so as to get closer to the patient or away thereof along said direction. In some embodiments, the target position for each of the detectors may be determined based on data indicative of distances between the patient and some or all of the plurality of detectors. For example, in some embodiments, in determining a target position of a certain detector, data indicative of the distances of the patient from the neighboring detectors, neighboring the certain detector, may be used.

In some embodiments, one, some, or each of the one or more gamma detectors involved in the scanning may have a respective 3D sensor mounted near it. For example, the 3D sensor may be mounted on a gantry where the arm carrying the gamma detector is supported, so that the 3D sensor is pointed at the patient along about the same direction as the gamma detector. In some embodiments, the field of view of each sensor is significantly larger than that of a detector, so the exact direction at which the sensor is aimed is less crucial. In another example, a 3D sensor may be mounted on the arm, e.g., inside a detection head comprising the gamma detector.

In some embodiments, two or more of the gamma detectors used in the method (for example, all of them) may be supported by a common gantry. In such embodiments, changing the angle from which a detector detects gamma radiation may include rotating the gantry and/or moving the patient in respect to the gantry.

In some embodiments, the determination of a target position for the gamma detector may include generating an approximation to the outer surface of the patient. The approximation may be based on data indicative of coordinates of a plurality of points on the outer surface of the patient and/or based on data indicative of distances of the patient from gamma detector(s) along a plurality of directions. For example, the approximation may provide approximated coordinates of any point of interest on the outer surface of the patient. Such approximation may be used for determining target position(s) to the gamma detector(s), for example, to determine limits for swiveling of the gamma detector(s), to determine a best position of the patient in respect of the gantry, to decide on angles from which gamma radiation is to be collected, etc. For example, in some embodiments it may be desired to have the center of the patient located at the center of the gantry (or shift from the center of the gantry by a predetermined amount). The location of the patient may be determined based on data indicative of coordinates of at least one point on the outer surface of the patient by estimating where the center of the patient is. The desired location of the patient may then be determined so that the centers of the patient and the gantry overlap or shift from one another as required. The determination or estimation of the location, for example the center, of the patient may include, for example, modeling the shape of the patient based on the data indicative of coordinates of surface points. The modeling may include, for example, interpolating and/or triangulating between surface points to build a continuous surface that models the outer surface of the patient (or the patient and support), whether in the context of center alignment or in any other context that requires determination or estimation of the location of the patient.

In some embodiments, the target position(s) may be determined based on data indicative of the kind of image to be taken, in addition to the distance between the patient and the detector, the coordinate of a point of the outer surface of the patient, or a combination of such distance and coordinates. The kind of image may include, for example, a region of interest, an organ of interest, a dimensionality of the image (e.g., 2D or 3D), etc. Examples to such embodiments are detailed below.

An aspect of some embodiments of the present invention may include an apparatus configured to carry out one or more of the scanning methods described herein. For example, the apparatus may include a gamma detector and a processor. The gamma detector may be mounted on an end of an arm extending towards the patient along a specified direction. In some embodiments, the arm may also be extendible along the specified direction. The processor may be configured to carry out a method as described herein. For example, the processor may be configured to: obtain data, indicative of a distance between the gamma detector and the patient along the specified direction. The data may be obtained from one or more 3D sensor(s), which may form part of the apparatus. The processor may be further configured to determine at least one target position for the gamma detector based on the data indicative of the distance. The processor may be further configured to cause the gamma detector to move to each of the at least one target position, and when at a target position, detect gamma radiation emitted from the patient. In some embodiments, the processor may be configured to move the patient, e.g., by moving a patient support, on which the patient or a portion of the patient body is supported. The movement may be of the patient in respect of the detector, of the detector in respect of the patient, or the patient and detector may both move in respect to each other.

An aspect of some embodiments of the invention includes automatically determining how to arrange the detectors near the outer surface of the patient to image a given region. In some embodiments, this automatic determination is based on data indicative of the region to be imaged, and a three dimensional approximation or model of the outer surface of the patient and the patient support (e.g., the patient and the bed). Throughout the specification, a bed is used as an example of a patient support, and a reference to a bed is to be understood as applying also to any other kind of support. For example, the data indicative of the kind of image to be taken (e.g., data indicative of the region of interest) may dictate a certain relation between the patient (or patient support) and the gantry. The data indicative of the kind of image to be taken and the corresponding relation between the patient or patient support and the gantry may be provided in the form of a lookup table.

In some embodiments, the determination is not of the arrangement of the detectors directly, but of some other one or more parameters that affect the detectors arrangement. For example, in some embodiments, such one or more parameters may include the position of the patient support (e.g., a position of a bed, on which the patient lies), in respect to the gantry. In another example, the parameters affecting the detectors' arrangement may include a rotation angle of the gantry.

In some embodiments, bringing a detector to the vicinity of the patient is by extending an arm on which a detection head comprising the detector is mounted. In some such embodiments, the detector may be made to controllably swivel in respect to the extendable arm on which the detection head is mounted. The swivel may allow changing an aim angle of the detector, e.g., without changing a gantry angle. In some embodiments, each detector may swivel independently of the other detectors. In swivel-enabled embodiments, the one or more parameters affecting the arrangement of the detectors may include the swivel angle of each detector in respect to the respective extendable arm.

In some embodiments, more than one arrangement of the detectors is determined for a single imaging process. For example, the imaging may include collecting photons with the gantry at a first gantry angle, and then collecting photons with the gantry at a second gantry angle. In some embodiments, each gantry angle may be associated with a time period for collecting photons. In some embodiments, the gantry may revolve smoothly along some angular range. In some embodiments, the one or more parameters determining the arrangement of the detectors include the angular range and/or one or more paces of going along the angular range.

Alternatively or additionally, the imaging may include collecting photons with the detectors at a plurality of different swivel angles. In some embodiments, the swivel angles may be controlled, e.g., using a rotary actuator; and the one or more parameters determining the detectors' arrangement may include the swivel angles and/or the time durations along which photons are collected at each swivel angle. In some embodiments, the detector may swivel smoothly along a range of swivel angles. In some embodiments, the one or more parameters determining the detectors' arrangement may include the range of swivel angles and/or the pace of going along said range. In some embodiments, each detector may be associated with a swivel angle monitor, for example, a magnetic encoder. This way, the actual angle at which the detector is aimed may be controlled, and not only the movement instructions provided to the detector.

As mentioned above, each of said parameters that may affect the detectors' arrangement in respect to the region to be imaged may be determined automatically based on two inputs: (1) what region is to be imaged; and (2) a model of the outer surface of the patient and bed (or other patient support). The model of the outer surface of the patient and bed may be generated based on input from one or more 3D sensors. The one or more 3D sensors may provide coordinates of at least one point of the outer surface of the patient and/or bed, and these coordinates may be used to model the outer surface.

Thus, an aspect of some embodiments of the invention includes a system for performing medical imaging of a region of interest in a patient. The system may determine a desired position of the patient in respect to a gantry. In some embodiments, the determination may be carried out automatically, that is, the user may instruct the system to determine the position, and the system carries out the determination without requiring any further input from the user. As used herein, the term gantry refers to a frame, which provides mechanical support for mounting the detector heads, such that the detectors can be positioned to scan a patient, or a part of the patient. In some embodiments, the gantry is cylindrical, and may be rotatable. In some embodiments of the invention, determining a desired position for the patient in respect to the gantry is carried out by the system, in some cases, without requiring the technologist attention. For example, the patient lies on a bed, a desired position for the bed is determined by the system, and the bed is moved to this desired position, in some embodiments, after a technologist confirmed such movement. In some embodiments, the patient support is static and the gantry moves to achieve the determined relative positioning between the patient support and the gantry. In some embodiments, the gantry is stationary and the patient support is moved. In some embodiments, both of patient support and gantry are moved in order to achieve the determined relative position.

In some embodiments, the imaging takes place with the patient lying on a bed, couch, or any other support. In some such embodiments, the system may determine a vertical positioning of the support. For example, if the couch is at a center of a gantry of the system, higher than the center, lower than the center, and by how far. Alternatively, or additionally, the system may determine a horizontal positioning of the support. For example, the system may determine where the gantry should be along a longitudinal axis of the patient.

In some embodiments, the imaging takes place with the patient sitting. For example, when imaging a leg, the patient may sit and the leg may be outstretched and supported by the patient support. In some embodiments, the imaging takes place with the patient in standing position, for example, for imaging under loading stress. The patient support may then have a form of a supporting wall and/or floor. In some embodiments, the body support may be a support for a breast. The body support may also be of any other kind or form.

In some embodiments, the system may include a computer programmed to determine the desired position of the support in respect to the gantry. To determine the desired positioning of the support, so that the patient himself is well positioned, it is useful to have information on the outer surface of the patient, and in some cases also of the support. Accordingly, in some embodiments of the present invention, the positioning (vertical and/or horizontal) is determined based on information regarding the outer surface of the patient and support. The information may include coordinates of one or more points on the outer surface of the patient (referred to herein as "surface points"). The computer may be programmed to estimate from the surface points a 3D structure of the outer surface of the patient (and support), and this 3D structure may provide basis for determining the desired position of the support. In some embodiments, the desired position may be determined directly from the coordinates of the surface points, without generating a model of the outer surface. The outer surface is also referred to herein as "contour", and the terms are used herein interchangeably.

The coordinates of the surface points may be received from one or more 3D sensors. Each of the 3D sensors can be any device that provides information of the spatial location of at least one point belonging to the outer surface of the patient and/or support. In embodiments of the present invention, the information is provided at well-defined physical units (e.g., cm or inches). The computer may be programmed to determine the desired positioning of the support in respect to the gantry based on the coordinates of the one or more surface points. In some embodiments, the computer may be programmed to estimate, based on the coordinates of the surface points, a 3D structure of the outer surface of the patient and support, and use this estimated structure to determine the desired positioning of the support in respect to the gantry.

For example, in some embodiments, there may be a desire to localize the center of the patient at the center of the gantry. This may be the case, for example, when an entire torso of the patient is to be scanned. In some such embodiments, the vertical positioning of the bed may depend on how large the patient is. With large patients, the front side of the body will be further from the support than with skinny patients. While one may not need an automatic measurement system to tell large from skinny, more delicate distinctions may be made by the system, allowing accurate positioning that in absence of information from the 3D sensor(s) may require several minutes of trial and error. For examples, in some embodiments, the determined position of the patient support brings the center of the patient to the center of the gantry (or to any other position in respect to the gantry) in accuracy of millimeters, e.g., 5, 2, 1, or 0.5 millimeter. Obtaining such accuracy with the system disclosed herein may save several minutes that would be required for positioning the patient using available means, even by the most experienced user. These minutes, saved with each patient, may allow more patients to benefit from imaging by the same device during a given time period.

In operation, according to some embodiments of the invention, before scanning begins, the patient lies on a bed, and the technologist enters to the computer an indication to a type of scan to be carried out. This indication may be provided by a user interface, which may include, for example, a touchscreen, a keyboard, and/or a barcode reader. In some embodiments, the type of scan may be retrieved from a database associating scan types with patients' identifiers. For example, the physician may enter into the personal file of the patient a scan request indicating the scan type. By scanning a barcode encoding a patient identifier (e.g., an ID or national insurance number of the patient), the kind of scan may be retrieved from the database. The technologist may, in some such cases, only verify that the patient he is dealing with is indeed the patient whose name is associated with the identifier.

The type of scan (also referred to herein as a scan type, scan kind, or kind of scan) may indicate, for example, the region of interest (e.g., liver, brain, a certain brain section, etc.), a scan category (e.g., planar, 3D, preview, etc.), the required quality (e.g., diagnostic or non-diagnostic), or a combination of any of these. The technologist may move the couch with the patient lying on it, so that the detector is roughly at the region to be imaged. Then, the user may send a control signal to the 3D sensor(s) to sense the outer surface of the patient and/or bed, and send coordinates of at least one surface point to the computer. The control signal may be sent by the user via the user interface. In some embodiments, a "start scanning" button may cause a control signal to be sent to the at least one 3D sensor. The at least one 3D sensor may be activated, at this or at any other stage of the imaging process, by the processor, without necessitating an explicit control signal to be initiated by the technologist.

The computer may determine the desired positioning of the patient's support based on the information received from the 3D sensors. For example, the computer may have a default instruction to bring the center of the patient to some predetermined location (e.g., the center of the gantry). The computer may determine the location of the center of the patient based on the coordinates of the at least one surface point. For example, the computer may be preprogrammed to fit a curve that approximates the patient's outer surface base on the coordinates of the at least one surface point, and approximate the center of the patient with a center of an area (or volume) defined by the fit curve.

In some embodiments, the scan type may also be used for determining a target for the relative positioning of the patient support and the gantry. This target may be referred to herein as a desired positioning. For example, the computer may be preprogrammed to bring the outer surface of the patient to the center of the gantry for scans of certain types (e.g., for planar scans), and bring the center of the patient to the center of the gantry at other scan types. It is to be noted that usually, information on the current position of the patient support is also available for the computer for determining the target positioning.

Once a desired positioning is determined, e.g., as described above, the computer may indicate this determination to the technologist. Such indication may be, for example, by displaying on a display a distance the patient support is to be moved (e.g., up or down), and/or an image symbolizing the patient supported by the support in the determined position, optionally in the environment of the gantry. The technologist confirms bringing the support with the patient thereon to the determined position, and a motor moves the bed to the position determined. In some embodiments, the confirmation is in response to an indication provided to the user by the system regarding the determined position. In some embodiments, the confirmation is given in advance, e.g., as a default. In some embodiments, the system automatically positions the patient support, without the need for operator confirmation.

In some embodiments, the user may indicate a body part desired to be scanned on the user interface, for example by selecting from a predefined list of body parts, or by selecting scan limits on a human avatar. In some embodiments, the body part desired to be scanned may be read from the patient file as mentioned above (e.g., after identifying the patient by reading a respective barcode). The system may then use input from the 3D sensors to get a model or point cloud of the patient, and analyze it to find the location of the body part to be imaged on the 3D model/point cloud. The processor may then position the bed at the desired location, in some embodiments, horizontal location, e.g., in response to a technologist confirmation.

DETAILED DESCRIPTION OF THE DRAWINGS

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Figure 1B:
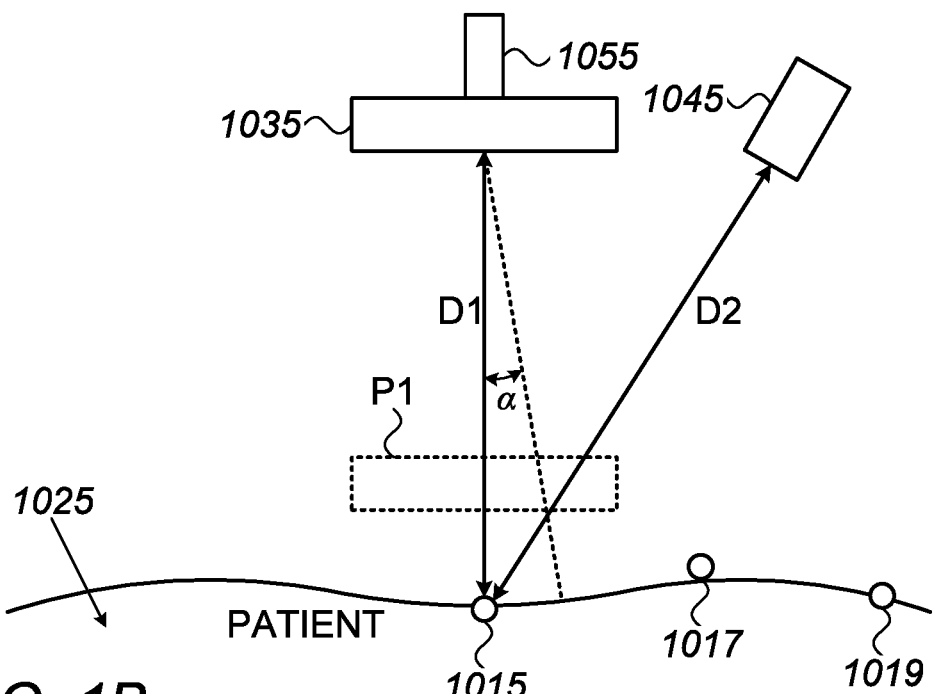
FIG. 1B is a diagram showing a portion of the patient, a gamma detector, a sensor, and some points and directions mentioned in the description of FIG. 1A.

FIG. 1A is a flowchart of a method 1000 of scanning at least a portion of a patient with a scanning apparatus comprising a gamma detector according to some embodiments of the invention. The gamma detector may be mounted on an arm extending towards the patient. FIG. 1B shows a portion of the patient (1025), a gamma detector (1035), a sensor (1045), and some points and directions mentioned in the description of method 1000. More detailed descriptions of gamma detectors are provided in FIG. 6A and FIG. 6B.

At 1010, data indicative of coordinates of points (e.g., 1015, 1017, 1019)) on the outer surface of the patient (1025) are obtained. The data indicative of the coordinates may be received from at least one 3D sensor (1045), and may include, for example, the coordinates themselves, in some coordinate system. In some embodiments, the coordinates may be provided in a coordinate system of the scanning apparatus. In some embodiments, the coordinates may be provided in a coordinate system of the detector (1035), the sensor (1045) or any other coordinate system that may be transformed to that of the scanning apparatus. In such embodiments, the data may be transformed to a coordinate system of the scanning apparatus, or any other coordinate system, allowing representation of the outer surface of the patient and the gamma detector on a common coordinate system.

In some embodiments, the data indicative of the coordinates of surface points of the patient may include data indicative of the coordinates in a less direct manner. For example, the data may include a distance D1 from the patient to the gamma detector along a specified direction. Such distance may allow computing the coordinates of a surface point based on the distance, the direction, and the coordinates of the gamma detector. Similarly, the data may include a distance D2 from the patient to a 3D sensor (1045) along a specified direction. Such distance may allow computing the coordinates of a surface point based on the distance, the direction, and the coordinates of the 3D sensor.

In another example, the data may be directly indicative to the coordinates of some points, and indirectly indicative to coordinates of some other points. For example, the data may include coordinates of some surface points (e.g., 1015, 1017). These surface points may be used for estimating coordinates of other surface points (e.g., 1019). The estimation may be based on an approximation, for example, interpolation, extrapolation, triangulation, and others. Under such circumstances, the data may be considered indicative of the coordinates of the other surface points estimated by approximation (e.g., 1019) as well as being indicative of coordinates of point(s) directly indicated (e.g., 1015, 1017).

In some embodiments, the gamma detector may be mounted on an arm (1055) extendible towards the patient. The extension direction of the arm may be the above-mentioned specified direction, for example, the data obtained in 1010 may be indicative of a distance between the gamma detector and a point on the outer surface of the patient along extension direction D1 of arm 1055. Data indicative of that distance may include, for example, the distance itself, other distances, that allow estimating an approximation to that distance, coordinates that allow calculation and/or estimation of that distance, etc.

At 1020, a target position is determined for the gamma detector. The target position may be determined based on the data obtained at 2010. For example, the obtained data may be indicative of the distance D1 between gamma detector 1035 and the patient along the extension direction of arm 1055. In some embodiments, the distance along that direction should be as small as possible without touching the patient. Thus, if data obtained at 2010 is indicative to that distance D1 is, for example, 25 cm, the target position determined at 1020 may be closer to the patient by 24.5 cm along the same line. If, however, the data obtained in 1010 indicates that at similar directions (e.g., directions that deviate from the extension direction of arm 1055 by an angle α smaller than a predetermined angle), the outer surface of the patient is closer to the gamma detector than at the extension direction of arm 1055, then the position may be determined to be further away from the patient (e.g., P1), so no point of the outer surface of the patient is touched. The avoided touch may be between the patient and the detector, or between the patient and a detection head comprising the detector, as described herein.

In some embodiments, the data obtained in 2010 is indicative to the distances of several points along the gamma detector from the patient. The distances may be along directions parallel to the extension direction of the arm, and the target position may be determined so that there is no contact between the patient and the detector at any of these points.

In some embodiments, a plurality of target positions may be determined at 1020 to a single gamma detector based on the data obtained at 1010. For example, the data obtained at 1010 may be used to determine a number of angular positions, at which the detector is to be detecting gamma radiation from the patient, for example, as described in FIG. 6A or FIG. 6B below. In another example, the data may be used to determine a plurality of swivel angles or a range of swivel angles, as described herein.

At 1030, the gamma detector (1035) is caused to detect gamma radiation from the patient when the gamma detector is at the target position. If more than one target position has been determined in 1020, the gamma detector may be caused to detect gamma radiation when it is in one or more of them. Causing the gamma detector to detect gamma radiation may include, for example, sending to the gamma detector a control signal, for example, from processor 108 discussed below. In some embodiments, the gamma detector may be controlled to move to the target position, and detect gamma radiation when it is at the target position. In some embodiments, the target position is characterized by the distance, position, and/or orientation of the detector in respect to the patient, or the portion of the patient that has to be imaged. The patient (or at least the portion to be imaged) may be moved in respect to the detector in addition to moving the detector, or instead of moving the detector. The patient or portion to be imaged thereof may be moved, in some embodiments, by moving a support supporting the patient or said portion thereof.

The movement of the detector may include extending the arm to get closer to the patient. In some embodiments, the movement may include changing a direction along which the arm is extended. For example, when the arm is supported on a gantry, the movement may include rotation of the gantry. The gamma detector may be controlled to settle at the target position, so that gamma radiation is detected when the detector is stable at its position. In some embodiments, a range of target positions may be determined, and the gamma detector may be controlled to move fluently along that range and detect the radiation during the movement. For example, when the target positions are arranged at different angles in respect to the patient (e.g., at different gantry angles), the detector may be moved around the patient (e.g., by rotating the gantry), and detect gamma radiation during this movement. In another example, when the target positions include a plurality of swivel angles, the detector may be controlled to swivel and detect gamma radiation during the swiveling. In some embodiments, swiveling and gantry rotation may be simultaneous.

In some embodiments, after a first target position is determined based on a first set of data (e.g., as in 1010 and 1020), the detector is moved to the first target position, and then data is obtained once again, and a second target position is determined. In some embodiments, no gamma radiation is detected when the gamma detector is at the first target position. Then, the detector may be moved to the second target position, and gamma radiation may be detected with the gamma detector at the second target radiation. In one example, such a process may be carried out when the first target position is characterized by a certain angular positioning of the arm (e.g., a gantry angle). When the detector is at the determined angular position, another set of 3D data may be obtained, for example, to determine a target position of the detector along the extension direction of the arm (which has changed in view of the first set of data obtained). Then, the gamma detector may be moved along that direction, e.g., by extending the arm to proper proximity to the patient.

In some embodiments, the scanning is carried out using two or more gamma detectors. The two or more gamma detectors may be operated to detect gamma radiation simultaneously (that is, at overlapping time periods), to save scanning time. Each of the gamma detectors may be mounted on an arm of its own, and its arm may extend towards the patient along a respective direction. In some such embodiments, the scanning method may include obtaining data indicative of a distance from the patient along the respective specified direction for each of the gamma detectors. Based on data indicative of at least some of these distances, a respective target position may be determined for each of the gamma detectors. Then, the gamma detectors may each be caused to detect gamma radiation from the patient at the respective target position.

In such embodiments, the interactions between the various detectors and/or arms are taken into consideration. For example, in some embodiments, each gamma detector is in a respective detection head, and the target position of each gamma detector is determined in consideration of target positions of other gamma detectors to ensure that the detection heads do not collide or otherwise interfere with each other.

In some embodiments, the method may include, in addition to receiving information as discussed in relation to 1010, receiving data indicative of the kind of image to be taken. Some such embodiments are discussed in more detail below.

FIG. 1C is a diagrammatic illustration of a system for performing medical imaging of a region of interest according to some embodiments of the invention. System 100 includes a support (102), a gantry (104), at least one 3D sensor 106, (4 3D sensors are shown) and a processor (108).

Support 102 is configured to support patient 110 during imaging. The patient support may be configured to support lying patients, as illustrated. In some embodiments, the patient support may be configured to support standing patients, sitting patients, and/or leaning patients. For example, the support may be horizontal, such as a patient bed, vertical, such as a wall or a back of a chair and the like. The support may be made of low attenuation material, for refraining from attenuating gamma radiation emanating from the patient towards the detectors on the other side of the support.

Gantry 104 includes a cylindrical frame that supports multiple detection heads 112. In some embodiments, in each detection head, the gamma detector faces support 102. An example of a detection head is described below in relation to FIG. 6A and FIG. 6B. Each detection head 112 may be mounted on an extendable arm 116, configured to take the detection head mounted on it in a linear in-out movement, so as to bring the detector closer to the patient or away of it. Gantry 104 is rotatable around an axis, along, for example, angle φ, to allow the gamma detectors to rotate around the support.

Each detection head 112 may include one or more gamma detectors, such as semiconductor radiation detectors, for example nuclear medicine (NM) detectors, for instance cadmium zinc telluride (CZT) detectors. A linear actuator is provided to linearly maneuver extendable arm 116 so that detection head 112 moves toward and from patient support 102 (also referred to herein as support 102). Optionally, the linear actuator is mechanical actuator that converts rotary motion of a control knob into linear displacement, a hydraulic actuator or hydraulic cylinder, for example a hollow cylinder having a piston, a piezoelectric actuator having a voltage dependent expandable unit, and/or an electro-mechanical actuator that is based on an electric motor, such a stepper motor and the like. In some embodiments, the linear actuator may include a stepper motor and a sensor, optionally a magnetic sensor (e.g., encoder) that senses the actual position of detection head 112, to provide feedback on the control of the stepper motor. The control of each linear actuator may be performed according to a scanning plan. In some embodiments, the scanning plan may be generated by processor 108.

Sensor 106 is a 3D sensor arranged to sense a portion of patient 110 when the patient is supported by support 102. Sensor 106 may be, for example, optical, ultrasonic, or based on radio waves or microwaves. Examples of specific technologies used in such sensors are structured light sensors, illumination assisted stereo sensors, passive stereo sensors, radar sensors, Lidar sensors, and time of flight sensors. Commercially available embodiments of such sensors include Microsoft Kinect, Intel® RealSense™ Camera F200, Mantis Vision's 3D scanners, PMD technologies PicoFlexx, and Vayyar imaging Wallabot. Sensor 106 is configured to output signals indicative of 3D coordinates of points (e.g., point 114, 114') on an outer surface of patient 110 and/or support 102. In some embodiments, the 3D sensor(s) provides a point cloud that allows approximating the outer surface of the bed and/or patient. In some embodiments, the 3D sensor may be installed on the gantry, as shown in FIG. 1. Alternatively or additionally, one or more 3D sensors may be installed on the extendable arm 116, inside detection head 112, on a separate support structure, or at any other location, at which the one or more 3D sensors can sense the position of at least one point of the outer surface of the patient and/or support.

Processor 108 may be configured to determine a desired position of support 102 in respect to gantry 104 based on data obtained by 3D sensors 106. As used herein, if a machine (e.g., a processor) is described as "configured to" perform a particular task (e.g., determine a desired position), then the machine includes components, parts, or aspects (e.g., software) that enable the machine to perform the particular task. In some embodiments, the machine may perform this task during operation. Processor 108 is diagrammatically described in FIG. 2. Processor 108 may include an input 202 configured to receive from 3D sensor 106 data indicative of at least one surface point 114. The data received from the processor may be raw data, convertible to 3D coordinates of the one or more surface points by processor 108 or any processing module connected to processor 108. In some embodiments, the 3D sensors may send the coordinates directly to processor 108. Data indicative of the 3D coordinates of the one or more surface points may be stored in memory 204. In some embodiments, memory 204 may store only the most update data received from sensors 106. In some embodiments, memory 204 may store the data for longer term, so as to allow further analysis of the data after imaging is concluded. This may help, for example, to correct for patient motion, and/or to identify in retrospect certain images of the outer surface of the patient as being taken at a certain point along a respiratory phase, for example, during exhale or inhale. Processor 108 may further include a memory 206 storing instructions for determining a desired position of the support in respect to the gantry based on the data received by the input. Memory 206 may be separate from memory 204, or may make part of memory 204. An example of a method by which processor 108 may determine the desired position is described in FIG. 3C. Processor 108 may further include a central processing unit (CPU) 208 configured to carry out the instructions saved on memory 206 using data stored on memory 204 and send results of the processing to output 210.

Output 210 may be connected to display 212. Display 212 may be, for example, a visual, audial, or visual-audial display. Display 212 may be configured to indicate to a user the desired position of the support in respect to the gantry, as determined by processor 108, based on input received at the display from output 210. In some embodiments, output 210 may be connected to a motor (not shown) configured to move support 102 to the determined position. The connection to the motor may be in addition to the connection to the display.

System 100 may also include a user interface 214. User interface 214 may allow the user (for example, a technologist) to indicate a kind of scan to be performed. The user interface may include, for example, a barcode reader to read a barcode attached to an imaging request for the patient. Optionally or alternatively, the user interface may include a keyboard, touchscreen, or any other input device allowing the user to indicate the kind of scan required. In some embodiments, details of the required scan may be inputted from another computer, e.g., through an intranet or through the Internet. Such input may be in addition to, or instead of, input from user interface 214. User interface 214 may also include at least one control for sending a control signal to the 3D sensor(s) to sense the outer surface of the patient and bed. In some embodiments, user interface 214 may also allow the user to confirm that the position determined by processor 108 is acceptable, and if such confirmation is received, the processor may control a motor to position the patient support according to the determination. In some embodiments, the display shows instructions for moving the patient support, and the user operates the motor manually according to the instructions. In some embodiments, after positioning (manual or automatic), the user may control the 3D sensor to sense the patient and bed once again, to verify that the position of the bed indeed brings the patient to the required position in respect of the gantry, and if not (e.g., because the patient moved), the process of determining and moving the bed may repeat until the positioning is satisfactory.

In some embodiments, processor 108 may be configured to have different or additional functions. For example, processor 108 may be configured (e.g., by proper programming) to generate a scanning plan. The scanning plan may be for imaging of at least a portion of a patient. In some embodiments, processor 108 may be configured to receive information indicative of the location of at least one point sensed by 3D sensor(s) 106, and generate the scanning plan based on the received information. In some embodiments, the processor may be further configured to receive information indicative of the type of scan, e.g., of the region to be scanned, and generate the scanning plan based on the type of scan and the location of the at least one point. The information indicative of the region to be imaged may be received by processor 108 from a user through user interface 214. In some embodiments, scanning plan may be generated based on a kind of scan. Kinds of scan are described herein. The terms type of scan, kind of scan, type of image, and kind of image, as well as image kind, image type, scan kind and scan type are used herein interchangeably.

The scanning plan may include, for example, a number of gantry positions and corresponding gantry angles. In some embodiments, the scanning plan may include a dwell time for each gantry position. In some embodiments, all the dwell times are planned to be of equal length. In some embodiments, two or more of the dwell times may differ from each other. Additionally to parameters pertaining to the gantry positions, or alternatively to such parameters, a scanning plan may include a plurality of swivel angles, for one or more of the detectors. In some embodiments, the plan may associate each of the swivel angles with a corresponding dwelling time. The dwelling times may be all equal, or they may include two or more dwelling times that differ from each other. Some considerations for determining gantry angles, swivel angles, and corresponding dwelling times are described herein.

In some embodiments, the scanning plan may include parameters for continuous scanning. For example, a first and second gantry positions and a rate of continuously advancing the gantry between said first and second gantry positions. In some embodiments, the rate of advancing the gantry between the first and second positions (or a plurality of rates each for a portion of the path between the two positions) may also be included in the scanning plan.

In some embodiments, the scanning plan may include a positioning of the support in respect of the gantry.

Figure 3A:
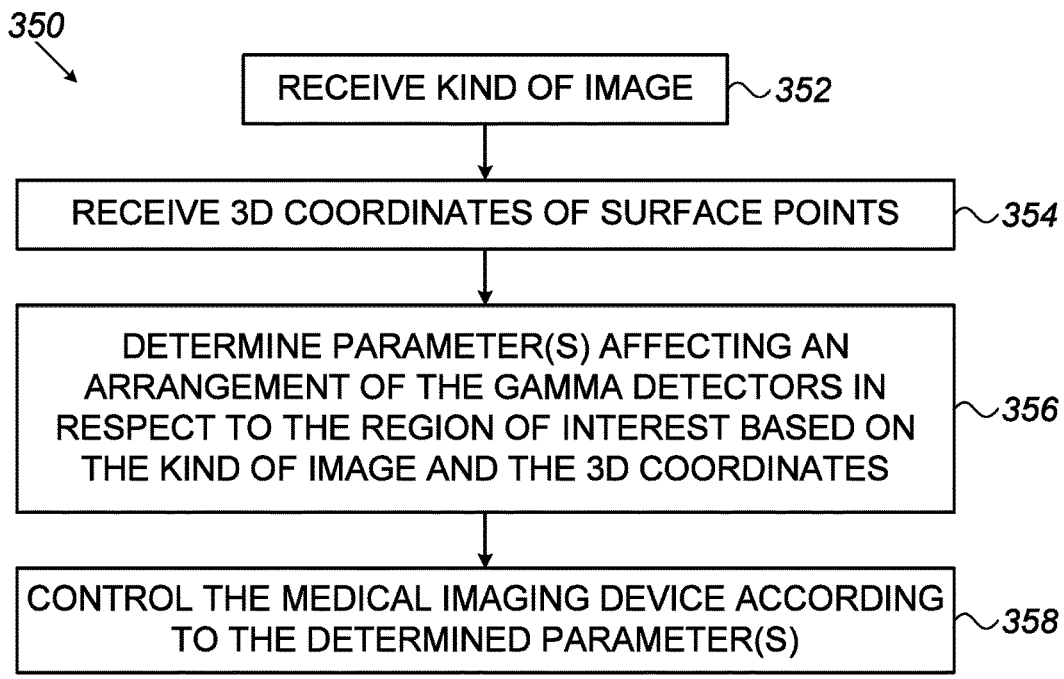
FIG. 3A and FIG. 3B are flowcharts of methods of imaging a region of interest in a patient according to some embodiments of the invention.

FIG. 3A is a flowchart of a method (350) of imaging a region of interest in a patient. The imaging may be by a medical imaging device comprising a plurality of gamma detectors supported on a gantry. The gantry may face a support for supporting the patient, or a portion of the patient, during imaging. The portion of the patient supported by the support may include the region of interest.

At 352, an indication of the kind of image to be taken is received. The kind of image may include, for example, the region of interest (e.g., brain or liver), the kind of scan (e.g., planar, 3D, preview, or dynamic planar preview), the required quality (e.g., diagnostic or non-diagnostic), or a combination of any of these.

At 354, coordinates of at least one point of an outer surface of the patient and/or support are received. The coordinates may be in the coordinate system of the medical imaging device. In some embodiments, the coordinates may be in physical units, for example, centimeters or inches.

At 356, at least one parameter affecting an arrangement of the gamma detectors in respect to the region of interest is determined based on the indication of the kind of image and the coordinates of the at least one point. The at least one parameter may include, for example, a position of the support in respect to the gantry, one or more gantry angles, and/or a range of gantry angles.

In some embodiments, each of the gamma detectors is mounted on an arm extendable from the gantry towards the support. The mounting may allow the gamma detector to swivel in respect to the arm. In such embodiments, the at least one parameter affecting the arrangement of the gamma detectors may include swivel angle of at least one of the detectors. The swivel angle may be determined in respect to the arm on which the respective detector is mounted. In some embodiments, the at least one parameter may include a plurality of swivel angles for one of the detectors, for some of the detectors, or for each of the detectors. In some embodiments, the at least one parameter may include a range of swivel angles. For example, each detector may have its own range of swivel angles, or some detectors may have a range of swivel angles and some only a single swivel angle, etc. In some embodiments, the ranges may differ from one another.

In some embodiments, the one or more parameters affecting the arrangement of the detectors may include a dwelling time for one or more of the positions. For example, a dwelling time for each gantry position, a dwelling time for each swivel angle, etc. may be determined for one or more of those parameters. The determination of the dwelling time may also be, in some embodiments, based on the coordinates of the point(s) of the outer surface of the support and/or patient. For examples, the coordinates may be used to spatially model the patient, and the dwelling times may be determined so that, in accordance with the model, longer dwelling times are associated with detector positions at which gamma radiation is collected from a thicker portion of the patient. In some embodiments, the dwelling times may be determined based on the scan type in addition to the coordinates of the surface points. For example, if the kind of image indicates a region of special interest (e.g., the pancreas), the location of the region of special interest may be estimated based on a model of the outer surface of the patient, and dwelling times for positions facing the region of special interest may be longer than dwelling times for positions facing other portions of the patient. For example, in some embodiments, a dwelling time may be determined for each gantry angle, and/or for each swivel angle of each detector. Similarly, in case the one or more parameters include a range of gantry angles, a pace by which the gantry is to be moved along the range may also be determined at 356. Similarly, in case the one or more parameters include a range of swivel angles for a detector, a pace by which the detector is to be moved along the range of swivel angles may also be determined at 356. The swivel pace may be determined similarly to dwelling times, with slow pace being determined under circumstances similar to those to which longer dwelling times are determined.

At 358, the gamma detectors, the gantry, and/or the support are controlled in accordance with the at least one parameter determined. For example, in some embodiments, processor 108 may send control signals to a motor that moves support 102 until the support is positioned at the position determined at 356. In another example, processor 108 may send control signals to a linear actuator that extends one of arms 116. Processor 108 may receive signals from a sensor that senses the position of the detector mounted on the arm 116, and keep sending control signals to the actuator until the signal received from the sensor indicates that the detector is at the position determined for it at 356. Similarly, processor 108 may send control signals to motors moving the gantry, and/or to motors that swivel each of the respective detectors, and verifies that the movement is in accordance with what's determined at 356.

Figure 3B:
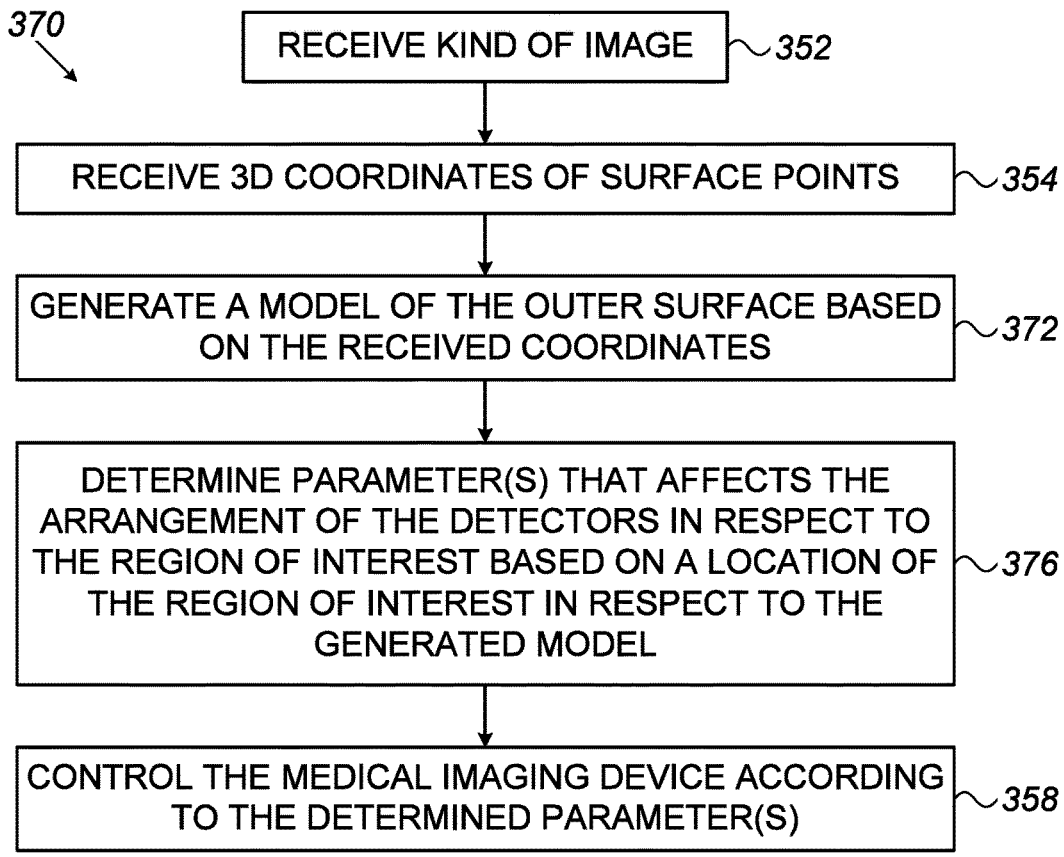

FIG. 3B is a flowchart of a method 370 similar to method 350 described above, but method 370 includes (at 372) generating a model of the outer surface of the patient and/or the support. The model may be generated based on the coordinates of the at least one point received at 354. In some embodiments, the model generated at 376 may be a 3D model of the outer surface of the patient and the bed. The term model may encompass any estimate of the structure of the outer surface of the patient and/or the bed. For example, in some embodiments, a general shape of the outer surface may be presumed (e.g., stored on a memory accessible to processor 108), and the exact dimensions of this general shape may be fit to the coordinates of the surface points, as these are received at 354. For example, the general shape may be provided as a parametric formula of a curve, and the values of the parameters may be found from the points by interpolation or by best fit methods.

In some embodiments, for example, when a rich point cloud is received from the 3D sensors, the model of the outer surface may be generated without presuming a general shape, but only by processing (e.g., by interpolation) the provided coordinates. In some embodiments, some knowledge of the shape (e.g., knowledge of the shape of the bed) may be used to help in generating the model.

In method 370, 356 may be replaced by 376, at which the at least one parameter that affects the arrangement of the detectors in respect to the region of interest is determined based on a location of the region of interest in respect to the model generated at 372. For example, when the region of interest is viewed in the context of the outer surface of the patient and bed, the outer surface may pose boundary conditions on the positioning of the detectors, and the shape of the region to be imaged may pose minimal requirements of coverage by the detectors.

Figure 3C:
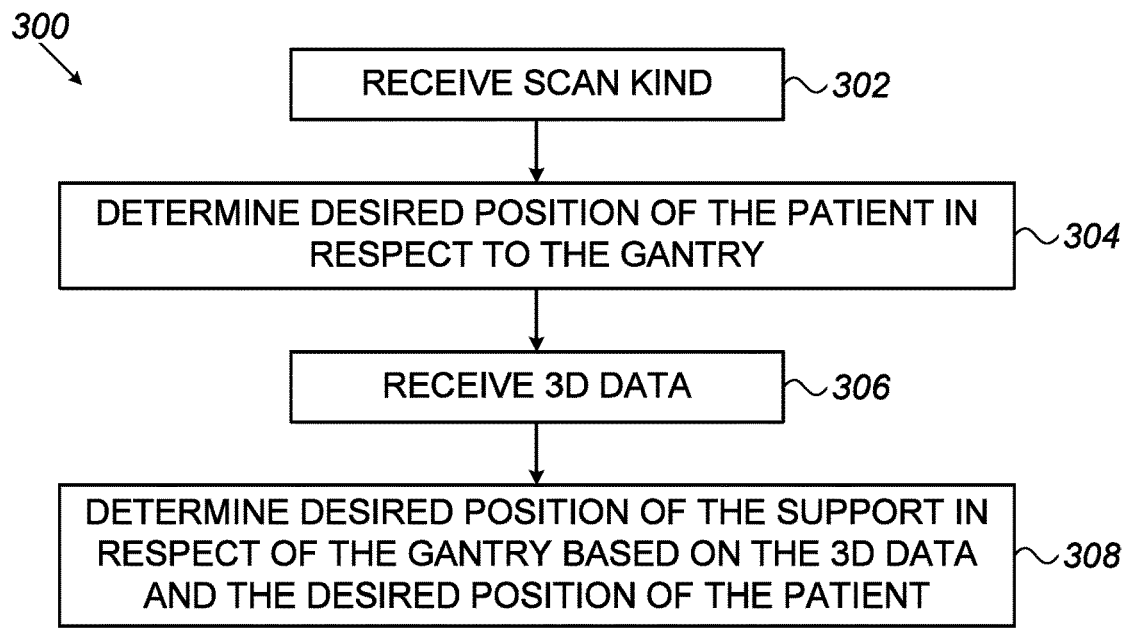
FIG. 3C is a flowchart of a method of determining a desired vertical position of a patient support according to some embodiments of the invention.

FIG. 3C is a flowchart of a method (300) of determining a desired vertical position of the patient support according to some embodiments of the invention.

At 302 a kind of scan is received, e.g., from user interface 214.

At 304 a position of the patient in respect of the gantry is determined based on the kind of scan. For example, in some embodiments, memory 206 may store a lookup table connecting each kind of scan with a desired position of the patient in respect of the gantry. In such a lookup table, some scan types may be associated with positioning the center of the patient at the center of the gantry. Some scan types (e.g., frontal planar scan) may be associated with positioning the frontal surface of the patient at the center of the gantry, or at any other predetermined position in respect to the gantry, for example, the position that allows maximal coverage of the front of the patient with detectors.

At 306 data from sensor(s) 106 is received.

At 308 the data received from the sensors is used to determine the position of the bed, at which the patient is at the required position in respect to the gantry. For example, if the kind of scan indicated via the user interface is associated with a target of bringing the center of the patient to the center of the gantry, the data received from the 3D sensor(s) is analyzed to find the center of the patient. If the kind of scan is associated with a target of bringing the front of the patient to where detectors can reach the front surface as close as possible without interfering with each other and without the patient or patient support hitting the gantry, the data from the 3D sensor(s) may be used for determining the position of the bed, at which this condition is achieved.

In some embodiments, the data received from the one or more 3D sensors 106 is used to generate a 3D model of the outer surface of the patient and the bed, or otherwise estimate the structure of the outer surface of the patient and the bed. For example, a general shape of the outer surface may be presumed, and the exact dimensions of this general shape may be fit to the coordinates of the surface points, as these are received from the 3D sensors. For example, the general shape may be provided as a parametric formula of a surface, and the values of the parameters may be found from the points by interpolation or by best fit methods.

In some embodiments, for example, when a rich point cloud is received from the 3D sensors, an approximation to the outer surface may be generated without presuming a general shape, but only by processing the provided points. The processing may include, for example, filtering the data, cleaning from outliers or other noisy data, and interpolating or triangulating the filtered/cleaned data. In some embodiments, some knowledge of the shape (e.g., knowledge of the shape of the bed) may be used to help in generating the approximation. In some embodiments, the approximation to the outer surface of the patient and/or support generated based on the coordinates of at least one surface point, may be used for determination of the at least one parameter that affects the arrangement of the detectors in respect to the region of interest.

The determination may be based on a location of the region of interest in respect to the model. For example, the model may set limitation on where the detectors may be positioned when determining positioning of the bed, gantry positions, swivel angles, etc. For example, the model may limit the detectors or the detector heads to be out of the outer surface, at some minimal distance from the face of a patient, etc.

In some embodiments, a quick, non-diagnostic, nuclear image may be taken by the gamma detectors, and based on that the positioning of the patient may be evaluated, to see if the current positioning is adequate or not. This may be useful particularly for the horizontal positioning along the longitudinal axis of the patient. If the imaging shows that some of the region of interest is outside the image, positioning is adjusted to correct for this.

Figure 4:
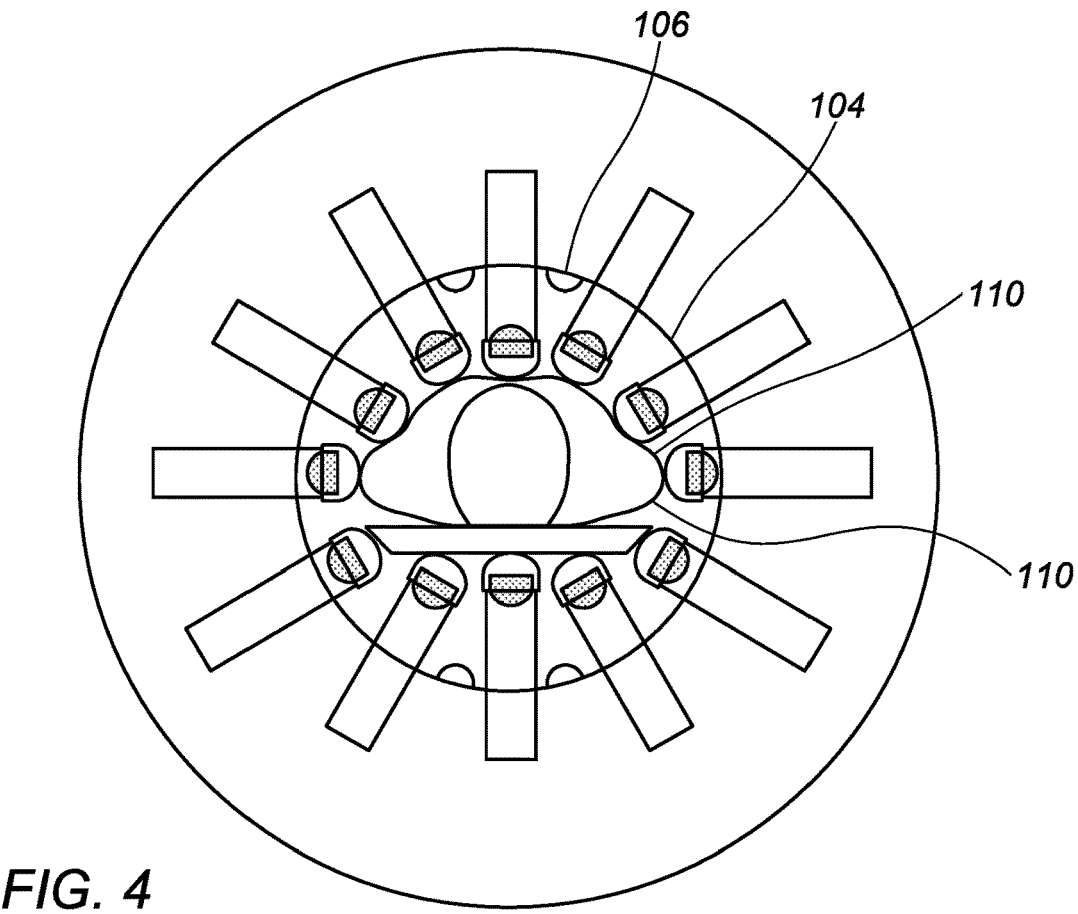
FIG. 4 is a diagrammatic illustration of a system with the patient at the center of the gantry according to some embodiments of the invention.

FIG. 4 is a diagrammatic illustration of a system according to some embodiments of the invention with a center (c) of a patient 110 at the center of gantry 104. The position of the center of the patient may have been determined by processor 108 based on data from 3D sensors 106. As can be seen in the drawing, all the detectors are as close as possible to the patient. This configuration may be suitable, for example, for imaging a region at the center of the patient (e.g., liver), for a general scan not particularly focused at any region inside the patient's body portion surrounded by the detectors, and in many others. As may be appreciated, although there are as many as 6 detectors that make good contact with the patient's body, the distances between them are quite large, and to obtain photons from the entire imaged region at all possible directions there may be a need to rotate gantry 104, so that data is collected at one or more additional gantry rotation angle(s). In the presently illustrated case, as there are 12 detectors, spaced from each other equally around the gantry, the angular difference between each two adjacent detectors is 30 degrees, and the additional gantry angle may be set 15 degrees from the present gantry angle.

Figure 5:
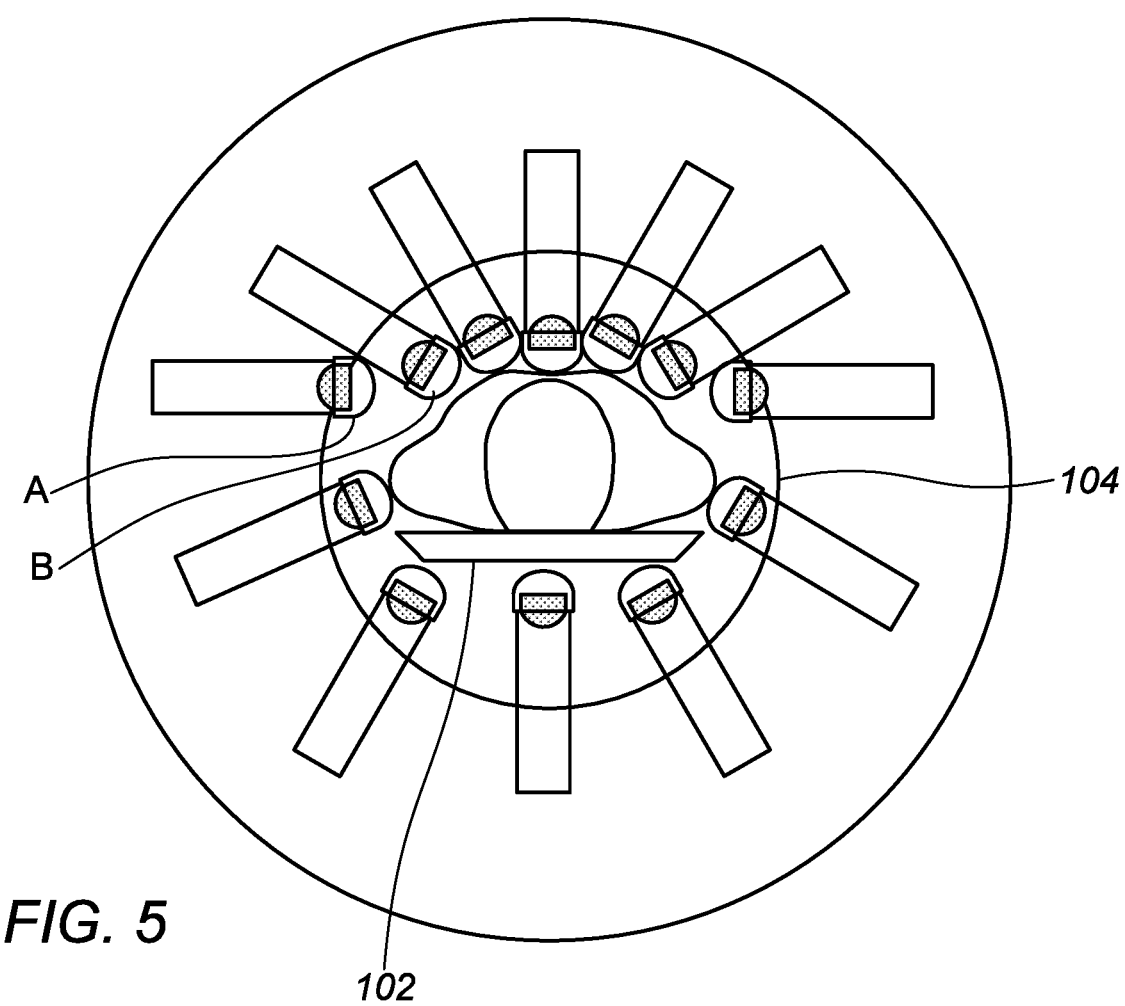
FIG. 5 is a diagrammatic illustration of a system with the patient off the center of the gantry according to some embodiments of the invention.

FIG. 5 is a diagrammatic illustration of the system and patient depicted in FIG. 4, however, in FIG. 5 the kind of image may be a frontal planar image, or any other image kind that would benefit from detectors that cover most closely the front part of the patient. In such a case, bed 102 may be lowered in gantry 104 so the extendable arms mounting the detectors that face the front side of the patient may be extended longer into the gantry than in FIG. 4, and cover the front side of the patient more densely than in FIG. 4. This way, collecting gamma photons from a single gantry angle may be enough in order to obtain a good imaging of the front of the patient. On the other hand, the contact between some of the detectors and the patient may be poorer than in FIG. 4. See, for instance, detectors A and B.

Figure 6A:
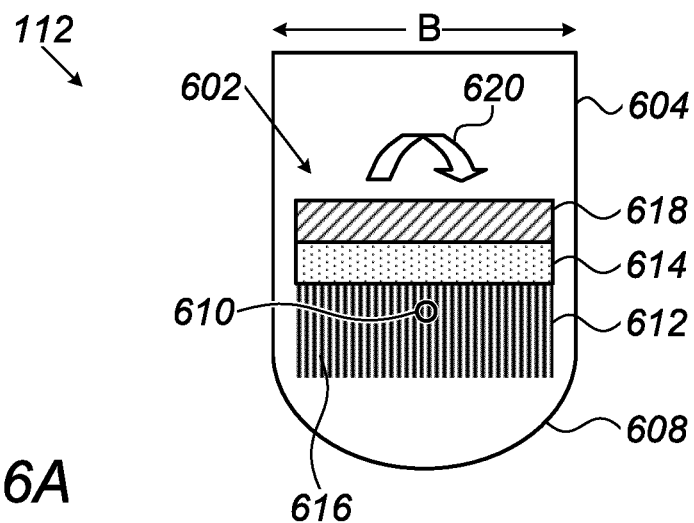
FIGS. 6A and 6B are two (mutually orthogonal) cross-sectional illustrations of a gamma detector according to some embodiments of the invention.

FIG. 6A is a cross-sectional illustration of a detection head 112 according to some embodiments of the invention. Detection head 112 has a breadth B, length L and height H (see FIG. 6B for the length L and height H). Detection head 112 may include a detecting unit 602 in a housing 604. For example, the detector units 602 may be housed to protect patient 110 from swivel motion (illustrated by the arrow 620) of the detecting unit 602. Housing 604 may have a round or curved cover. In some embodiments, housing 604 includes a cover shaped with a section 608 of a cylinder that allows for the swivel of the detecting unit 602 around a swiveling axis 610. Detection head 112 is shown to include a parallel hole collimator 612. Such a collimator may be used to gain information about the direction from which each photon arrives at the detection layer 614. Collimator 612 may include thin walls 616 (also referred to as septa) that define channels parallel to each other. The walls may be made of materials that have high linear attenuation coefficient for gamma radiation, such as lead or tungsten. Each photon may be considered to arrive to a point where it hits detection layer 614 through a channel of the collimator. Most of the photons that hit septa 616 are absorbed by the septa, so that mainly photons that go nearly perpendicularly to detection layer 614 reach the detection layer. The near perpendicularity may be expressed as a solid angle, from which the photons have to emerge in order to have a high probability (e.g., larger than 90%) to reach the detection layer. Detecting unit 602 may also include a heat sink (618), which may be attached to the detection layer on the detection layer side free of collimator 612. Detection head 112 may also include electronics (not shown) for transferring data to and from the detection layer to processor 108.

While the explanations above refer to a collimator known in the field as a parallel hole collimator, one or more of collimators 612 may be of a different kind, for example, a pinhole collimator, a slant hole collimator, or a fan beam collimator (e.g., a converging collimator, or a diverging collimator). In some embodiments, different detectors 112 may include collimators of different kinds.

Detection head 112 may include further parts, as well known in the field. For example, the detection layer 614 may include a plurality of detection modules, and each may have its own ASIC (Application Specific Integrated Circuit). The detection head may further include a carrier board which holds all of the detection modules, and interfaces to the ASICs. The detection head may also include shielding from external radiation, additional mechanics to hold the detection layer, ASICs, electronics, cover, etc., together. The detection head may also include a swivel motor, a swivel axis, belt, tensioners, encoder for encoding the exact swivel angle, electronic boards to control the motion of the detector (with the detection head and/or inside the detection head), and electronic boards to transfer data indicative of the photons received at the detection layer.

Figure 6B:
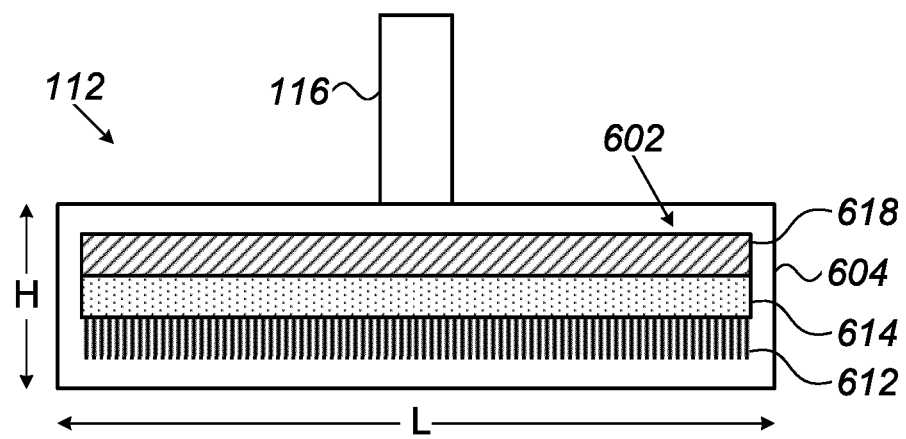

FIG. 6B is a cross-sectional illustration of the detection head shown in FIG. 6A along a cross-section perpendicular to that depicted in FIG. 6A. FIG. 6B illustrates that in some embodiments detection head 112 may be elongated, for example, to almost contact with the patient along a line parallel to the longitudinal axis of the patient. The length of detector 602 may be sufficient to allow acquiring the entire scan without moving the patient (or the gantry) along the patient, and yet short enough to allow maximal proximity between the detector and the patient taking into account body curvatures. A length of about 30 cm to 40 cm is found to be satisfactory for imaging grown up humans. FIG. 6B also shows extendable arm 116 (not shown in FIG. 6A). In some embodiments, the angle between extendable arm 116 and detector 602 is fixed, e.g., as 90°. In some embodiments, the angle between extendable arm 116 and detector 602 may be controllable, e.g., by processor 108. In some embodiments, the length of detector 602 is about 30 cm, the length of the outer cover is about 40 cm, and the radius of curvature of the round part 608 of cover 604 is about 5 cm. The length of the cover may extend beyond the length of the detector, for example, to allow accommodation of electronics, encoders, and/or proximity sensors, (all not shown).

Figure 7A:
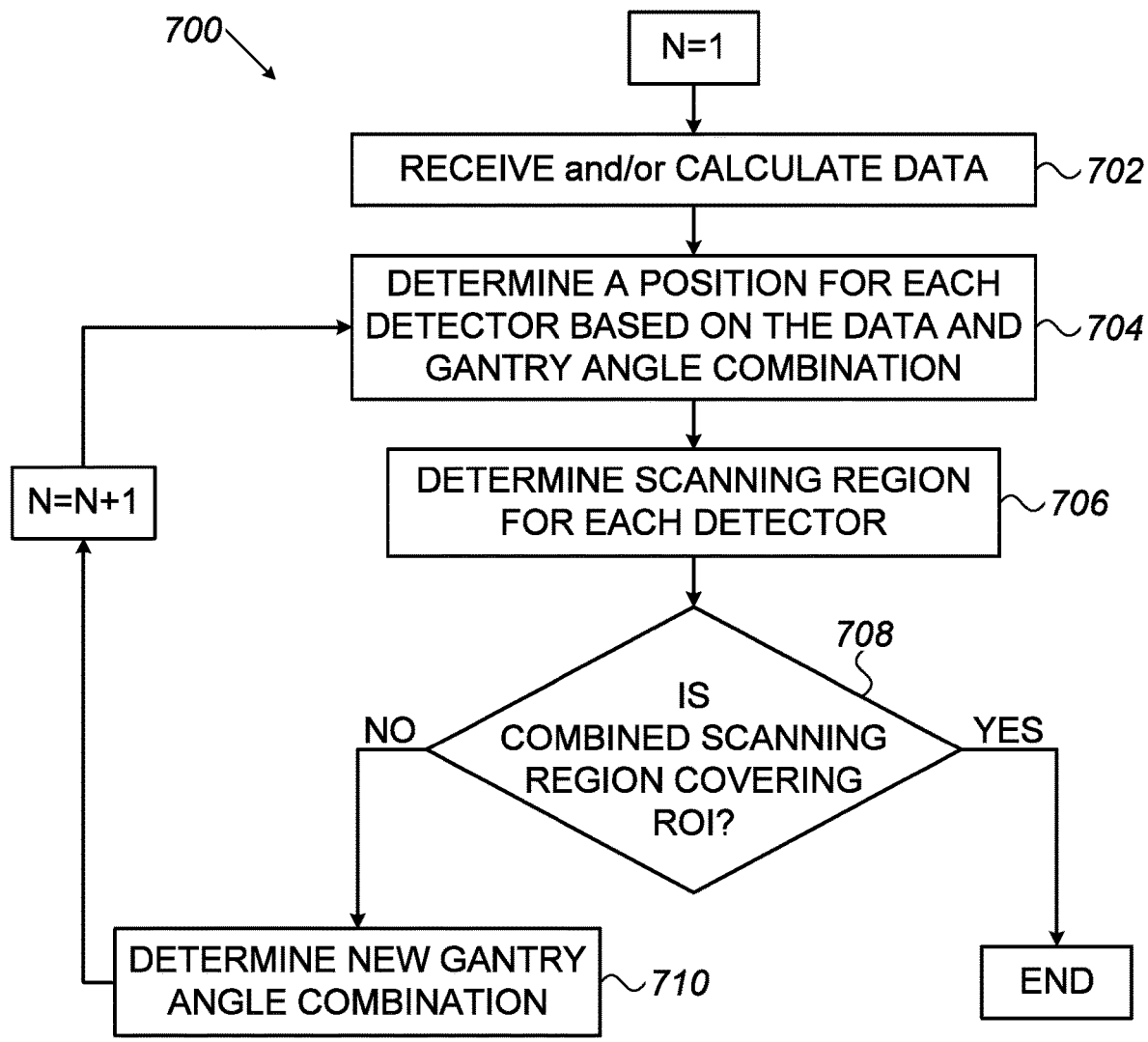
FIG. 7A is a flowchart of a method of determining gantry angles according to some embodiments of the invention.

FIG. 7A is a flowchart of a method 700 for determining gantry angles according to some embodiments of the invention.

At 702, data indicative of the outer surface of the bed and patient in respect to the gantry may be received. Alternatively or additionally, the data or part thereof may be calculated based on information on the position of the bed (e.g., as determined in method 300) and information indicative of the outer surface of the bed and patient received from the 3D sensors.

At 704, a position is determined for each one of the detection heads based on the outer surface of the bed and patient in respect to the gantry, and a gantry combination.

The angular position of each detection head is determined based on a gantry angle. A set of gantry positions required to accomplish a certain scan may be referred to herein as a gantry combination. Method 700 may determine a gantry combination iteratively. For example, at a first iteration, there may be a default gantry combination, for example, a combination made of a single gantry position at some angle referred to herein as 0 degrees. At subsequent executions of step 704 the gantry combination may include more than one gantry position. In method 700 the number of gantry positions in a combination (N) increases by one at each execution of step 704. In other embodiments (not shown), several different combinations of the same number of gantry positions may be tried. In some embodiments, the angular distance between adjacent gantry positions composing a single gantry combination may be equal. Thus, when the angular distance between two adjacent detection heads is 45 degrees, the first combination will include the gantry at angle 0, the second combination will include the gantry at angles 0 and 22.5 degrees, the third combination will include the gantry at angles 0, 15, and 30 degrees, etc.

Figure 7B:
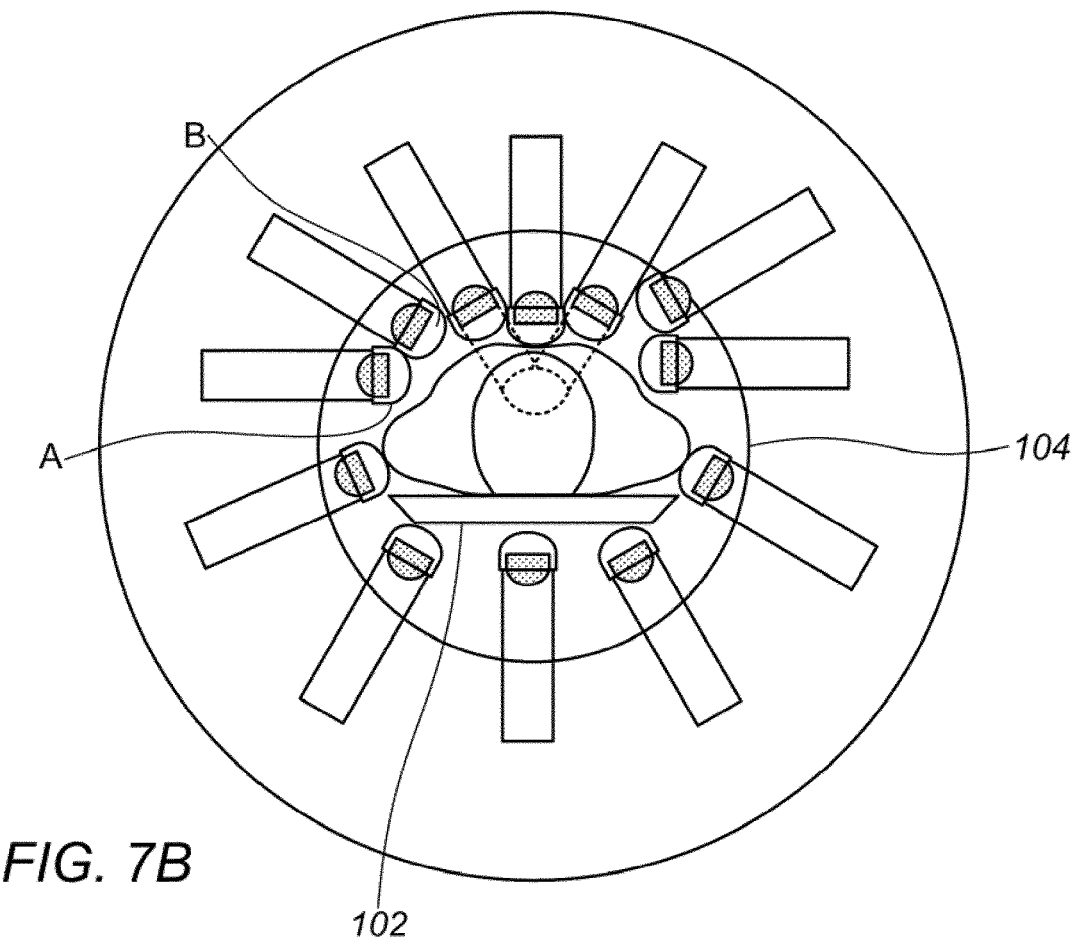
FIG. 7B is a diagrammatic illustration of a system with the patient off the center of the gantry, with the detectors arranged differently than in FIG. 5, according to some embodiments of the invention.

The radial position of each detector may be determined as that, in which each detector is as close as possible to the patient. Finding these positions may take into account interactions between different detection heads, for example, such that at each time, each portion of the space around the patient can be occupied by no more than one detection head. In some embodiments, an approximation of the outer surface may be generated (e.g., by fitting an analytical curve to the one or more points received from the 3D sensor), and the position of the detection heads are determined so that each detection head is as close as possible or tangent to the fit curve. In some cases, when one detection head may hinder the movement of another detection head (e.g., when the patient is not at the center of the gantry), the processor may determine at 704 which detector is to be closer to the patient, and which is left further from the patient, or decide that both detectors are at similar, intermediate distance from the patient. For example, in FIG. 5 it was decided to take detector B as close as possible to the patient and leave detector A further from the patient outer surface. In another embodiment, shown in FIG. 7B, a different choice is made. Here, detectors A and B are positioned both away of the patient, but at similar distances, while in FIG. 5 detection head B almost touches the patient, and detection head A is much further.

At 706 a scanning region is determined for each of the detectors. In some embodiments, a scanning region may be the region from which the detector can collect photons while swiveling the detection unit through all possible swivel angles.

At 708 it is checked if the entire region to be imaged is covered from a sufficient number of directions to facilitate the required image quality by a combination of the scanning regions of all the detectors in all the gantry angles composing the gantry combination. The sufficient number of directions may be, for example, directions spanning 180°. If so (708: Yes), no further gantry combination need to be assessed, the number N of gantry positions to be practiced during the imaging is determined, and the process ends. If portions of the region to be imaged are outside the combined scanning regions of all the detectors at all the gantry positions composing the gantry combination, (708: No), an additional gantry combination is to be assessed. At 710 this additional gantry composition is determined, the number N is increased by 1, and the method may continue to 704.

In some embodiments, the swivel angles at which each detector collects photons may be determined for a given combination of gantry positions. Finding these swivel angles may be determined by a standard optimizing procedure under the adequate constrains. For example, in some embodiments, an equal time is devoted for photon collection at each swivel angle, and the optimization procedure is run to find the swivel angles that allow spending a minimal amount of time at each of the gantry positions. In an alternative embodiment, the optimization procedure is run to find the swivel angles that allow imaging the entire region to be imaged at minimal imaging time. In some embodiments, the number of swivel angles used at each of the detectors is set to be equal, and this setting is used as a constraint on the optimization procedure.

In the above discussion it is assumed that gantry angles and swivel angles are controlled discretely. However, in some embodiments, the gantry angles, the swivel angles, or both, may be controlled to change continuously and fluently. This may save imaging time that otherwise would be spent stabilizing the system after each and every event at which the gantry or any of the detectors stop moving. Reconstructing images from moving detectors is generally known in the art of SPECT. Finding the limits of gantry continuous rotation may be found, for example, as described in method 700, but once the gantry composition is found, the gantry angles change fluently between the first and last gantry position included in the gantry composition. For example, if the gantry composition determined by method 700 includes the gantry positioned at angles of 0, 10, and 20 degrees, the continuous movement may be between 0 and 20 degrees. Swivel ranges may be determined similarly, for example, by finding necessary swivel angles as described above, and then moving fluently along angular ranges defined between the two most distanced swivel angles defined for each detector. In some embodiments, when swivel angles are changed continuously, the swivel rate of each detector is determined so that all the detectors begin and end swiveling together, so a detector that swivels along a broader range swivels faster than a detector that swivels along a narrower range.

In some embodiments, each swivel angle is associated with dwelling time (also referred to as a dwell time), along which gamma photons are collected with the detector at the respective swivel angle. In some embodiments, the dwell times may be all of equal length. In some embodiments, two or more of the dwell times may differ from each other. In some embodiments, the dwelling times may be determined so that when a detector looks at a thicker portion of the patient the dwelling time is longer than when the detector looks at a thinner portion of the patient. For example, looking at the two horizontally mounted detectors in FIG. 4, which almost touch the patient's shoulders. When the detectors are aimed as in the figure, they collect photons from an extremely thick portion of the patient's body, extending from one shoulder to the other. However, when theses detectors are swiveled a little down (e.g., to face the edge of the bed), they collect photons from a very thin portion of the patient. Therefore, in some embodiments, the dwelling time at the latter swivel angle is much shorter than the dwelling time at the former one. Dwelling times may be determined based on data indicative of coordinates of at least one surface point by modeling the outer surface of the patient and support based on the data indicative of the coordinates, and determining the dwelling times using the thickness of different portions of the model, so that if, according to the model, a detector faces at a first position a thicker portion of the patient that at a second position, the dwelling time at the first position will be longer than the dwelling time at the second position.

In some embodiments, each gantry angle is associated with dwelling time, along which the gantry is static at the respective gantry angle. The gantry-angle related dwelling times may all be the same, or may include two or more mutually different dwelling times. The dwelling time of the gantry angle may be determined based on the longest dwelling time associated with any of the detectors. A dwelling time associated with a detector may include a summation of the dwelling times associated with all the swivel angles of the detector.

Figure 7C:
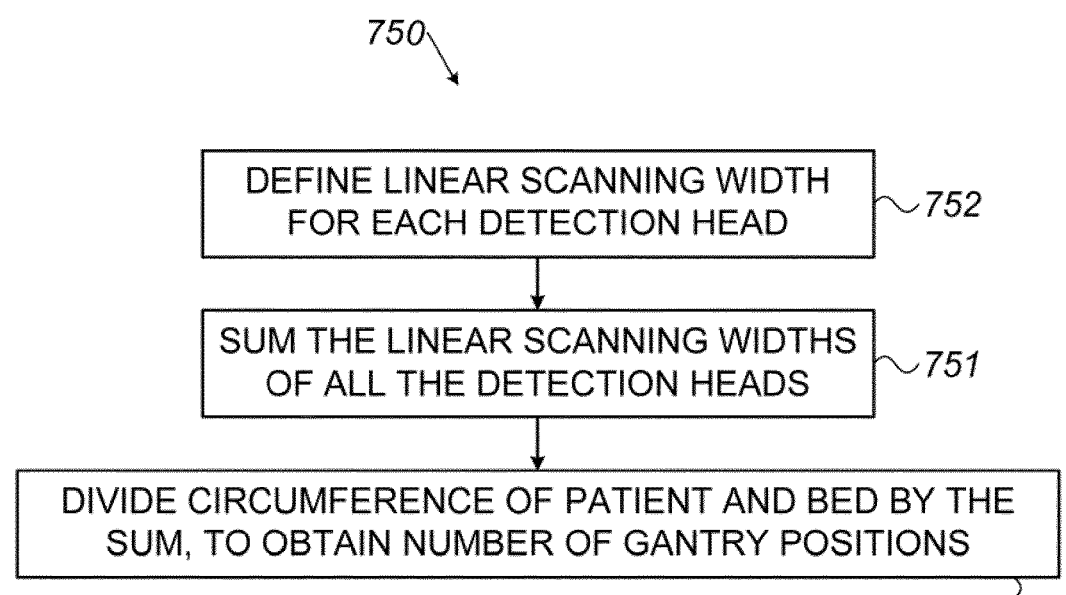
FIG. 7C is a flowchart of a method for determining gantry angles according to some embodiments of the invention.

FIG. 7C is a flowchart of a method 750 for determining gantry angles according to some embodiments of the invention. In some embodiments, this may be a calculation of a lower bound on the number of gantry positions, and may be used as a starting point in FIG. 7A instead of naively starting with 1 as described there.

At 752 a linear scanning width is defined to each detector. In some embodiments, the linear scanning width may equal the breadth B of the detector (illustrated in FIG. 6A). In some embodiments, the linear scanning length is defined before scanning begins. For example, it may be preprogrammed into processor 108.

At 751, the linear scanning width of all the detectors is summed. In case all the detectors are associated with the same linear scanning width, this width is multiplied by the number of detectors.

At 756, the number of gantry positions is determined as the quotient obtained by dividing an approximation of a circumference of the patient and the patient support by the sum of linear scanning widths obtained at 751, to obtain a number of gantry positions. If the number of gantry positions so obtained is not a whole number, it may be rounded, for example, to the nearest whole number.

The approximation of the circumference may be obtained from coordinates of the at least one surface point provided by the 3D sensor as described herein.

Aspects of some embodiments of the invention include systems and methods for generating a scanning plan. The scanning plan may be for medical imaging of at least a portion of a patient. In some embodiments, such a system includes a processor configured to receive input data, and generate based on the input data a scanning plan. The input data may include, for example, an indication of a region to be imaged; and data indicative of the location of at least one surface point located on an outer surface of the portion of the patient to be scanned. The location of the surface point may be sensed by one or more 3D sensors, as described above. The processor may be configured to generate the scanning plan based on the received information. The scanning plan may include, for example, gantry angles, corresponding dwelling times, swivel angles for each detector, dwelling times corresponding to the swivel angles, a range of gantry angles to be swept continuously, etc, as a function of time, for example a succession of respective dwelling times for a sequence of gantry angles and/or a succession of respective dwelling times for a sequence of swivel angles. Other examples include a range of (gantry and/or swivel) angles and a rate of change for the angles, respective angular trajectories defined by a continuous function or discrete samples over time. Of course, a scanning plan may comprise any combination of one or more of these ways to define angular trajectories. More generally, a scanning plan may define respective angular trajectories for gantry and/or swivel angles. In some embodiments, the scanning plan uses as additional input the positioning of the patient support. The positioning may be vertical and/or horizontal. In some embodiments, the processor is configured to determine the positioning of the bed with respect to the gantry before or as part of generating the scanning plan. In some embodiments, a system for generating a scanning plan includes a gantry, detectors, patient support, and other structural parts related to each other as described above in reference to system 100.

In some embodiments, the system for generating the scanning plan may include only the processor, with input or inputs to receive the required information and an output to deliver the scanning plan, e.g., for evaluation by a user or for execution by an imaging apparatus capable of controlling all the various parameters to be controlled in accordance with the plan. The system may also be composed of the processor and some or all of the parts of system 100.

In some embodiments, the planning may be updated during scanning. For example, in some embodiments, a preliminary scanning plan may be generated based on a first point cloud generated by the one or more 3D sensors. During the execution of the plan, the one or more 3D sensors may be exposed to other part of the patient, e.g., because the patient moved, or because the sensor(s) moved. For example, in embodiments where the sensors are mounted on the gantry, changing a gantry angle may change the body portion exposed to the sensors. In another example, where the sensors are mounted on the extendable arms, taking the arms nearer or further from the patient may expose different portions of the patient to the sensors. Such further exposure may provide data useful for better planning of the scan.

Figure 8:
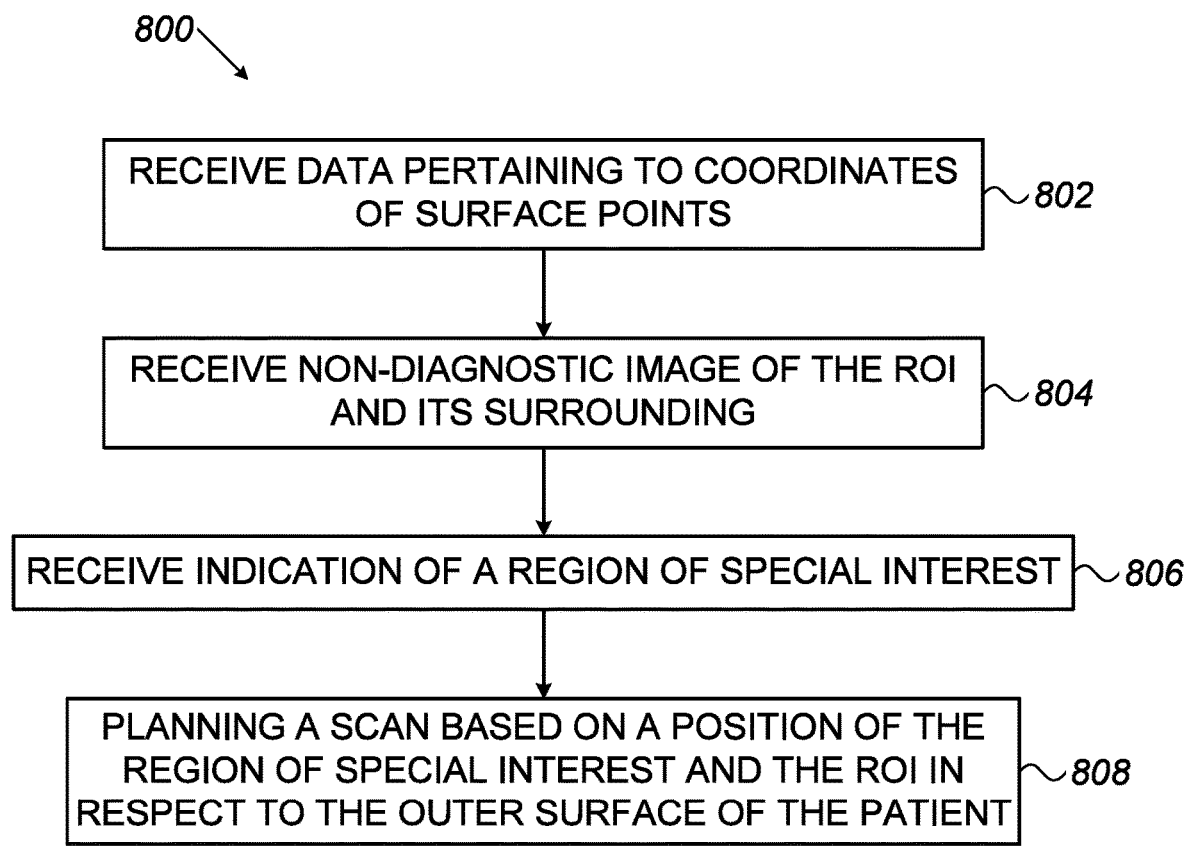
FIG. 8 is a flowchart of a method of planning a scan of a region to be imaged according to some embodiments of the invention.

FIG. 8 is a flowchart of a method 800 of planning a scan of a region to be imaged residing in a portion of a patient by a medical imaging device. The medical imaging device may include a support, such as a bed or a couch. The support may be configured to support at least the portion of the patient that has to be imaged. The imaging device may further include multiple gamma detectors facing the support. The detectors may be all supported by a gantry, which may be rotatable.

At 802, data pertaining to spatial coordinates of a point of an outer surface of the portion of the patient is received. In some embodiments, the spatial coordinates are of a plurality of points composing a point cloud indicative of the position of an outer surface of the patient's portion to be imaged, the support supporting said patient's portion, or both the patient and the support. For example, in some embodiments, the data may include coordinates of a plethora of points, forming together a point cloud that visually resembles the outer surface of the patient's portion to be imaged, and/or of the bed, on which the patient portion to be imaged is supported. The data pertaining to the spatial coordinates of the one or more points of the outer surface of the patient may be received from a 3D sensor as described herein. The data may include coordinates of one point, two points, or more points. For example, the data may include coordinates of points composing a point cloud indicative of the position of an outer surface of a portion of the support and/or patient.

In some embodiments, the data is received from a plurality of 3D sensors. In such cases, data from different sensors may be combined to provide a combined point cloud. The combined point cloud may provide data on points from all portions of the outer surface of the patient and/or bed (e.g., if the fields of view of the 3D sensors cover, when combined, the entire outer surface), or portions thereof (e.g., when there are gaps between fields of view of adjacent sensors). The received data may be indicative of the spatial coordinates of the surface points in the coordinate system of the medical imaging device, or in some other coordinate system that can be registered to the coordinate system of the medical imaging device. In the latter case, the method may include a step of registering the data to the coordinate system of the device. This step may include, in some embodiments, calibration of the system. Combining data sets received from different 3D sensors may be carried out after this registration or calibration. For example, the sensors may be calibrated each to its own coordinate system, e.g. the received point cloud is in units of mm with regard to an arbitrary coordinate system, as determined by the sensor manufacturer. In such cases, a systemic calibration may be performed, where several calibration objects are placed in known locations within the coordinate system of the scanning system. The calibration objects may be imaged by each sensor, and the location may be detected within the sensor's coordinate system. Once the location of the calibration objects is known in the sensor coordinate system, a transformation between the coordinate system of the 3D sensor and that of the scanning system may be determined. This transformation may be a rigid transformation. Each time the sensor is used during normal operation, the coordinates provided by the sensor may be transformed to the scanning system coordinates using the said transformation. In some embodiments, the calibration may be repeated at different sensor locations, e.g., at different gantry angles. In some embodiments, one calibration is used, and the calibrated coordinates are transformed to reflect the movement of the sensors.

In some embodiments, based on the data pertaining to the coordinates of the surface points, a non-diagnostic scan may be planned, for example, as described herein. The non-diagnostic scan is then carried out.

At 804, the non-diagnostic radiographic image of the portion of the patient is received. The dimensionality of the radiographic image may be the same as the dimensionality of the image to be taken. For example, if the image to be taken is planar, so is the non-diagnostic radiographic image; and if the image to be taken is 3D, so is the non-diagnostic radiographic image. The non-diagnostic radiographic image may be, for example, a planar view of a certain plane in the patient's portion to be imaged, or a 3D image having a low signal to noise ratio. The non-diagnostic image may be of the patient's portion to be imaged. The non-diagnostic image may include the region to be imaged and its immediate surrounding. The non-diagnostic image may be acquired by less than half a time that an image of diagnostic quality may be acquired. For example, the non-diagnostic image may be acquired in less than 10 minutes, for example, in one or two minutes.

At 806, an indication of a region of special interest is received. The indication may be put in by a user, of example, by marking a region on a display of the non-diagnostic image.

At 808, a diagnostic scan is planned based on the location of the region of special interest, and the data pertaining to coordinates of the surface points. For example, in some embodiments, collecting gamma photons is planned to take place from every point within the outer surface; but the plan may include devoting more time to collecting gamma photons emerging from the region of special interest than from other regions that are to be scanned. Thus, longer dwelling times may be associated in the scanning plan to swivel angles at which a detector is aimed at the region of special interest than in other swivel angles. In some embodiments, however, some time is devoted to collecting photons emerging from points outside the region of special interest to allow a more accurate reconstruction of the image.

More generally, the scanning plan may include any parameter that may affect the arrangement of the detectors in respect of the region to be imaged, such as vertical positioning of the bed in the gantry, horizontal positioning of the bed in the gantry, gantry angles to be used, and swivel angles to be used. In some embodiments, the plan may also include timing instructions, for example, the dwell time for each detector at each swivel angle and the dwell time of the system at each gantry angle. One, some, or all of these may be determined so as to maximize image quality while minimizing imaging time, taking into consideration the exact position of the region of special interest, as revealed from the marking made on the non-diagnostic image, and constraints originating from the location of the outer surface of the patient, as revealed by the one or more 3D sensors.

It is expected that during the life of a patent maturing from this application many relevant systems and methods will be developed and the scope of the term image, scanning, and directable detector is intended to include all such new technologies a priori.

As used herein the term "about" refers to ±10%.

The terms "comprises", "comprising", "includes", "including", "having" and their conjugates mean "including but not limited to".

As used herein, the singular form "a", "an" and "the" include plural references unless the context clearly dictates otherwise. For example, the term "a processor" or "at least one processor" may include a plurality of processors, separated from each other or interconnected in any conceivable form.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The invention claimed is:
1. A system for medical imaging a region of interest, the system comprising:

a support, for supporting at least a portion of a patient's body;
a gantry, supporting a gamma detector;
a 3D sensor; and
a processor,
wherein
the processor is configured to:
receive an indication of the kind of image to be taken;
receive from the 3D sensor coordinates of at least one point of an outer surface of the patient, the support, or both the patient and the support; and
determine a plurality of gantry angles based on the coordinates of the at least one point and the kind of image to be taken.

2. The system of claim 1, wherein the indication of the kind of image to be taken comprises an indication of the region of interest.

3. The system of claim 1, wherein the processor is further configured to determine a position of the support in respect to the gantry based on the coordinates of the at least one point and the kind of image to be taken.

4. The system of claim 1, wherein the processor is further configured to determine, based on the indication of the kind of image to be taken and the coordinates of the at least one point, a respective dwelling time for each of said plurality of gantry angles.

5. The system of claim 1, wherein the plurality of gantry angles are determined in the form of a range of gantry angles.

6. The system of claim 5, wherein the processor is further configured to determine, based on the indication of the kind of image and the coordinates of the at least one point, a pace for moving the gantry along the range of gantry angles.

7. The system of claim 6, wherein the processor is configured to determine, based on the indication of the kind of image and the coordinates of the at least one point, a plurality of different paces, each for moving the gantry along a sub-range of the range of gantry angles.

8. The system of claim 1, wherein each of said gamma detectors is mounted on an arm extendable from the gantry.

9. The system of claim 1, wherein each of said gamma detectors is arranged to swivel in respect to an arm connecting the gamma detector to the gantry.

10. The system of claim 9, wherein the processor is further configured to determine a swivel angle of the detector in respect to the arm for at least one of the detectors based on the coordinates of the at least one point and the kind of image to be taken.

11. The system of claim 9, wherein the processor is further configured to determine a range of swivel angles of the detector in respect to the arm for at least one of the detectors based on the coordinates of the at least one point and the kind of image to be taken.

12. The system of claim 11, wherein the processor is further configured to determine, based on the indication of the kind of image and the coordinates of the at least one point, a pace for moving the detector along the range of swivel angles.

13. The system of claim 9, wherein the processor is further configured to determine, based on the indication of the kind of image and the coordinates of the at least one point, an amount of extension of at least one extendable arm connecting a gamma detector to the gantry.

14. The system of claim 1, wherein the processor is configured to generate, based on the coordinates of the at least one point, a model of the outer surface of the patient, the support, or both the patient and the support, and determine the plurality of gantry angles based on a location of the region of interest in respect to the model.

15. The system of claim 12, wherein the processor is configured to determine at least one parameter affecting the arrangement of the gamma detectors in respect to the region of interest, in addition to the range of swivel angles, based on a location of the region of interest in respect to the model of the outer surface of the patient and/or support.

16. A method of imaging a region of interest in a patient by a medical imaging device for imaging a patient supported by a patient support, the medical imaging device comprising a gantry and a plurality of gamma detectors supported on the gantry, the method comprising:
receiving an indication of the kind of image to be taken;
receiving coordinates of at least one point of an outer surface of the patient, the support, or both the patient and the support;
determining a plurality of gantry angles based on the indication of the kind of image and the coordinates of the at least one point; and
controlling the gamma detectors, the gantry, and/or the support in accordance with the plurality of gantry angles determined.

17. The method of claim 16, wherein a position of the support in respect to the gantry is also determined based on the indication of the kind of image and the coordinates of the at least one point.

18. The method of claim 16, further comprising determining, based on the indication of the kind of image to be taken and the coordinates of the at least one point, a respective dwelling time for each of said plurality of gantry angles.

19. The method of claim 16, wherein the plurality of gantry angles is determines determined as a range of gantry angles.

20. The method of claim 19, further comprising determining, based on the indication of the kind of image to be taken and the coordinates of the at least one point, a pace for moving the gantry along the range of gantry angles.

21. The method of claim 16, wherein each of said gamma detectors is mounted on an arm extendable from the gantry so that the gamma detector may swivel in respect to the arm.

22. The method of claim 21, wherein a swivel angle of a detector in respect to the arm is also determined based on the indication of the kind of image and the coordinates of the at least one point.

23. The method of claim 22, wherein a plurality of swivel angles of a detector in respect to the arm for at least one of the detectors is also determined based on the indication of the kind of image and the coordinates of the at least one point.

24. The method of claim 23, wherein the plurality of swivel angles includes a range of swivel angles.

25. The method of claim 24, further comprising determining, based on the indication of the kind of image and the coordinates of the at least one point, a pace for moving the detector along the range of swivel angles.

26. The method of claim 16, wherein an amount of extension of at least one extendable arm connecting a gamma detector to the gantry is also determined based on the indication of the kind of image and the coordinates of the at least one point.

27. The method of claim 16, further comprising generating, based on the coordinates of the at least one point, a model of the outer surface of the patient, the support, or both the patient and the support, and determining the plurality of gantry angles based on a location of the region of interest in respect to the model of the outer surface of the patient and/or support.

* * * * *